US007989182B2

(12) United States Patent
Mulley et al.

(10) Patent No.: US 7,989,182 B2
(45) Date of Patent: Aug. 2, 2011

(54) NUCLEIC ACID ENCODING SCN1A VARIANT

(75) Inventors: John Charles Mulley, Firle (AU);
Louise Anne Harkin, Northgate (AU);
Leanne Michelle Dibbens, College Park (AU); Robyn Heather Wallace, Memphis, TN (US); Hilary Anne Phillips, Port Noarlunga (AU); Sarah Elizabeth Heron, Highbury (AU); Samuel Frank Berkovic, Caulfield North (AU); Ingrid Eileen Scheffer, Malvern East (AU)

(73) Assignee: Bionomics Limited, Thebarton, SA (AU)

( * ) Notice: Subject to any disclaimer, the term of this patent is extended or adjusted under 35 U.S.C. 154(b) by 0 days.

(21) Appl. No.: 12/696,769

(22) Filed: Jan. 29, 2010

(65) Prior Publication Data

US 2010/0136623 A1 Jun. 3, 2010

Related U.S. Application Data

(62) Division of application No. 10/482,834, filed as application No. PCT/AU02/00910 on Jul. 8, 2002, now abandoned.

(30) Foreign Application Priority Data

Jul. 18, 2001 (AU) .................................. PR6452
Mar. 5, 2002 (AU) .................................. PS0910
May 13, 2002 (AU) .................................. PS2292

(51) Int. Cl.
*C07H 21/02* (2006.01)
*C07H 21/04* (2006.01)
*C12N 15/00* (2006.01)
*C12N 15/12* (2006.01)
*C12N 1/21* (2006.01)
*C12N 1/19* (2006.01)

(52) U.S. Cl. ................... 435/69.1; 435/71.1; 435/320.1; 435/252.3; 536/23.5; 536/24.3; 530/350

(58) Field of Classification Search .................. None
See application file for complete search history.

(56) References Cited

U.S. PATENT DOCUMENTS

| 4,016,043 | A | 4/1977 | Schuurs et al. |
| 4,172,124 | A | 10/1979 | Koprowski et al. |
| 4,474,893 | A | 10/1984 | Reading |
| 4,971,903 | A | 11/1990 | Hyman |
| 5,331,573 | A | 7/1994 | Balaji et al. |
| 5,579,250 | A | 11/1996 | Balaji et al. |
| 6,331,614 | B1 | 12/2001 | Wong et al. |
| 7,078,515 | B2 | 7/2006 | Wallace et al. |
| 7,282,336 | B2 | 10/2007 | Wallace et al. |
| 7,709,225 | B2 | 5/2010 | Wallace et al. |
| 7,723,027 | B2 | 5/2010 | Petrou et al. |
| 2003/0157525 | A1 | 8/2003 | Mintier et al. |
| 2004/0096886 | A1 | 5/2004 | Rouleau et al. |
| 2004/0110706 | A1 | 6/2004 | Wallace et al. |
| 2004/0214195 | A1 | 10/2004 | Rouleau et al. |
| 2004/0229257 | A1 | 11/2004 | Petrou et al. |
| 2005/0074764 | A1 | 4/2005 | Mulley et al. |
| 2006/0089306 | A1 | 4/2006 | Wallace et al. |
| 2006/0252121 | A1 | 11/2006 | Wallace et al. |
| 2009/0081724 | A1 | 3/2009 | Mulley et al. |
| 2010/0088778 | A1 | 4/2010 | Mulley et al. |
| 2010/0136623 | A1 | 6/2010 | Mulley et al. |
| 2010/0203548 | A1 | 8/2010 | Petrou et al. |

FOREIGN PATENT DOCUMENTS

| AU | 656247 | 6/1996 |
| WO | WO84/03564 | 9/1984 |
| WO | WO97/02048 | 1/1997 |
| WO | WO 01/38564 | 5/2001 |
| WO | WO01/88125 | 11/2001 |
| WO | WO01/98486 | 12/2001 |
| WO | WO 02/06521 | 1/2002 |
| WO | WO 02/50096 | 6/2002 |
| WO | WO03/008574 | 1/2003 |
| WO | WO 2004/085674 | 10/2004 |
| WO | WO 2005/014863 | 2/2005 |

OTHER PUBLICATIONS

GenBank Accession No. AC0100127, NCBI Database, National Center for Biotechnology Information, National Library of Medicine, NIH (Bethesda, MD, USA), GI: 11597116, May 9, 2001.*
GenBank Accession No. AC0100127, NCBI Database, National Center for Biotechnology Information, National Library of Medicine, NIH (Bethesda, MD, USA), GI: 11597116, Apr. 8, 2005.*
Verma et al., Nature, 1997, vol. 389, pp. 239-242.*
Orkin et al. "Report and Recommendation of the Panel to Assess the NIH Investment in Research on Gene Therapy", NIH, 1995.*
Thomas et al. Nature. 2003. 4: 346-358.*
Abstracts of Decisions. Decision of a Delegate of the Commissioner of Patents corresponding to an Australian Patent Application No. 18465/01 issued Jan. 29, 2007.
Alekov et al., "A sodium channel mutation causing epilepsy in man exhibits subtle defects in fast inactivation and activation in vitro," *Journal of Physiology*, vol. 529, No. 3, pp. 533-539 (2000).
Andermann, "Multifactorial Inheritance of Generalized and Focal Epilepsy," Genetic Basis of the Epilepsies, pp. 355-374 (1982).
Annegers, "The Epidemiology of Epilepsy," The Treatment of Epilepsy: Principles and Practice, Chpt. 11, pp. 165-172 (1996).
Baulac et al., "A Second Locus for Familial Generalized Epilepsy with Febrile Seizures Plus Maps to Chromosome 2q21-q33," Am. J. Hum. Genet., vol. 65, pp. 1078-1085 (1999).
Bell and Lathrop, "Multiple loci for multiple sclerosis," Nature Genetics, vol. 13, pp. 377-378 (Aug. 1996).

(Continued)

*Primary Examiner* — Carla Myers
(74) *Attorney, Agent, or Firm* — Jenkins, Wilson, Taylor & Hunt, P.A.

(57) ABSTRACT

A method of identifying a subject predisposed to a disorder associated with ion channel dysfunction, comprising ascertaining whether at least one of the genes encoding ion channel subunits in said subject has undergone a mutation event such that a cDNA derived from said subject has the sequence set forth in one of SEQ ID NOS: 1-134.

5 Claims, 3 Drawing Sheets

OTHER PUBLICATIONS

Berkovic et al., "Concepts of absence epilepsies: Discrete syndromes or biological continuum?" Neurology, vol. 37, No. 6, pp. 993-1000 (Jun. 1987).

Berkovic et al., "Familial Epilepsies in Israel: Clinical Syndromes and Modes of Inheritance," Neurology, vol. 54, Suppl. 3, A356, No. P05.063 (Apr. 2000).

Berkovic et al., "The epilepsies: specific syndromes or a neurobiological continuum?" Epileptic Seizures and Syndromes, Chpt. 5, pp. 25-37 (1994).

Bertille Hille, "Ionic Channels of Exciteable Membranes," $2^{nd}$ Edition, pp. 423 and 434-444 (1992).

Bertrand et al., "Properties of neuronal nicotinic acetylcholine receptor mutants from humans suffering from autosomal dominant nocturnal frontal lobe epilepsy," British J. of Pharmacology, vol. 124, pp. 1-10 (1998).

Bievert et al., "A Potassium Channel Mutation in Neonatal Human Epilepsy," Science, vol. 279, pp. 403-406 (Jan. 16, 1998).

Bourgeois, "Chronic Management of Seizures in the Syndromes of Idopathic Generalized Epilepsy," Epilepsia, 44 (Suppl. 2), pp. 27-32 (2003).

Breaker et al., "A DNA enzyme with Mg2+-dependent RNA phosphoesterase activity," Chemistry and Biology, vol. 2, No. 10, pp. 655-660 (1995).

Cannon, "Sodium Channel Gating: No Margin for Error," Neuron, vol. 34, pp. 853-858 (Jun. 13, 2002).

Cavazzuti et al., "Longitudinal Study of Epileptiform EEG Patterns in Normal Children," Epilepsia, vol. 21, pp. 43-55 (1980).

Charlier et al., "A pore mutation in a novel KQT-like potassium channel gene in an idiopathic epilepsy family," Nature Genetics, vol. 18, pp. 53-55 (Jan. 1998).

Chou et al., "The lack of association between febrile convulsions and polymorphisms in SCN1A," Epilepsy Research, vol. 54, pp. 53-57 (2003).

Claes et al., "De Novo Mutations in the Sodium-Channel Gene SCN1A Cause Severe Myoclonic Epilepsy of Infancy," American Journal of Human Genetics, vol. 68, pp. 1327-1332 (2001).

Cole et al., "Human monoclonal antibodies," Molecular and Cellular Biochemistry, vol. 62, pp. 109-120 (1984).

Collins, "Positional cloning moves from perditional to traditional," Nature Genetics, vol. 9, pp. 347-349 (Apr. 1995).

Commission on Classification and Terminology of the International League Against Epilepsy, "Proposal for Revised Classification of Epilepsies and Epileptic Syndromes," Epilepsia, vol. 30, No. 4, pp. 389-399 (1989).

Communication pursuant to Rule 46(1) EPC corresponding to European Application No. 04718885.9-2402 PCT/AU2004000295 dated Jul. 14, 2006.

Cote et al., "Generation of human monoclonal antibodies reactive with cellular antigens," Proceedings of the National Academy of Sciences of the USA, vol. 80, pp. 2026-2030 (1983).

Doose and Baier, "Genetic aspects of childhood epilepsy," Cleveland Clinic Journal of Medicine, vol. 56, Suppl. Part 1, S101-5110.

Doose and Baier, "Genetic Factors in Epilepsies with Primarily Generalized Minor Seizures," Neuropediatrics, vol. 18, Suppl. I, pp. 1-64 (Feb. 1987).

Dworakowska and Dolowy, "Ion channels-related diseases," ACTA Biochimica Polonica, vol. 47, No. 3, pp. 685-703 (2000).

Escayg et al., "Mutations of SCN1A, encoding a neuronal sodium channel, in two families with GEFS+2," Nature Genetics, vol. 24, pp. 343-345 (Apr. 2000).

Escayg et al., "A Novel SCN1A Mutatin Associated with Generalized Epilepsy with Febrile Seizures Plus- and Prevalence of Variants in Patients with Epilepsy," Am. J. of Hum. Genet., vol. 68, pp. 866-873 (2001).

European Patent Office Search Report dated Apr. 10, 2007 for European Patent Application No. 07075566.52401.

Examiner's First Report for Australian Patent Application No. 2004200978 dated May 6, 2004.

European Patent Office Search Report corresponding to European Patent Application No. 07075566.5-2401 dated Oct. 4, 2007.

European Patent Office Search Report corresponding to European Patent Application No. 04718885.9-2402 PCT/AU2004000295 dated Jul. 14, 2006.

Finkelstein et al., "Use of denaturing gradient gel electrophoresis for detection of mutation and prospective diagnosis in late onset ornithine transcarbamylase deficiency," Genomics, vol. 7, pp. 167-172 (1990).

Fong et al., "Childhood Absence Epilepsy with Tonic-Clonic Seizures and Electroencephalogram 3-4-Hz Spike and Multispike—Slow Wave Complexes: Linkage to Chromosome 8q24," Am. J. Hum. Genet. vol. 63 pp. 1117-1129 (1998).

Fujiwara et al., "Mutations of sodium channel a subunit type 1 (SCN1A) in intractable childhood epilepsies with frequent generalized tonic-clonic seizures," Brain, vol. 126, pp. 531-546 (2003).

Fukuma G., "Mutations of neuronal voltage-gated Na+ channel alpha 1 subunit gene SCN1A in core severe myoclonic epilepsy in infancy (SMEI) and in borderline SMEI (SMEB)," Epilepsia, vol. 45, No. 2, pp. 140-148 (Feb. 2004).

Gardiner, "Impact of our understanding of the genetic aetiology of epilepsy," J. Neurol., vol. 247, pp. 327-334 (2000).

GeneCards output for protein-coding SCN1A, available online from www.genecards.org, pp. 1-20.

GenBank Locus NM_006920, "Homo sapiens sodium channel, voltage-gated, type I, alpha (SCN1A), mRNA," pp. 1-11 (Nov. 13, 2006).

GenBank Locus AF225985, "*Homo sapiens* voltage-gated sodium channel alpha subunit SCN1A (SCN1A) mRNA, complete cds," pp. 1-4 (Feb. 1, 2001).

Gennaro et al., "Familial severe myoclonic epilepsy of infancy: truncation of $Na_v1.1$ and genetic heterogeneity," Epileptic Disord., vol. 5, pp. 21-25 (2003).

Geysen H.M. et al., "Cognitive features of continuous antigenic determinants," Journal of Molecular Recognition, vol. 1, pp. 32-41 (1988).

Goldman et al., "In vitro and in vivo gene delivery mediated by a synthetic polycationic amino polymer," Nature Biotechnology, vol. 15, pp. 462-466 (1997).

Goldsby et al., "Immunology," Fifth Edition, section "Cross-Reactivity," p. 141 (2003).

Gonzalez et al., "Cell-based assays and instrumentation for screening ion-channel targets," Drug Discovery Today, vol. 4, No. 9, pp. 431-439 (1999).

Greenberg et al., "Evidence for multiple gene loci in the expression of the common generalized epilepsies," Neurology, vol. 42, Suppl. 5, pp. 56-62 (Apr. 1992).

Greenberg et al., "Juvenile Myoclonic Epilepsy (JME) May be Linked to the BF and HLA Loci on Human Chromosome 6," Am. J. of Medical Genetics, vol. 31, pp. 185-192 (1988).

Greenberg et al., "Segregation Analysis of Juvenile Myoclonic Epilepsy," Genetic Epidemiology, vol. 5, pp. 81-94 (1988).

Hamill et al., "Improved patch-clamp techniques for high-resolution current recording from cells and cell-free membrane patches," Pflügers Archiv European Journal of Physiology, vol. 391, pp. 85-100 (1981).

Harkin et al., "The Spectrum of SCN1A-Related Infantile Epileptic Encephalopathies," Brain, vol. 130, pp. 843-852 (2007).

Haseloff et al., "Somple RNA enzymes with new and highly specific endoribonuclease activities," Nature, vol. 334, No. 18, pp. 585-591 (1988).

Hauser et al., "Incidence of Epilepsy and Unprovoked Seizures in Rochester, Minnesota: 1935-1984," Epilepsia, vol. 34, No. 3, pp. 453-468 (1993).

Heller et al., "Discovery and analysis of inflammatory disease-related genes using cDNA microarrays," Proceedings of the National Academy of Sciences of the USA, vol. 94, pp. 2150-2155 (1997).

Hirchhorn et al., "A comprehensive review of genetic association studies," Genetics in Medicine, vol. 4, No. 2, pp. 45-61 (2002).

Huse et al., "Generation of a large combinatorial library of the immunoglobylin repertoire in phage lambda," Science, vol. 246, pp. 1275-1281 (1989).

International Search Report for PCT/AU2004/000295 dated May 14, 2004.

Interview Summary and Official Communication corresponding to U.S. Appl. No. 11/262,647 dated Dec. 5, 2008.

Interview Summary corresponding to U.S. Appl. No. 10/806,899 dated Nov. 1, 2007.
Interview Summary corresponding to U.S. Appl. No. 10/806,899 dated Nov. 23, 2009.
Interview Summary corresponding to U.S. Appl. No. 10/806,899 dated Oct. 8, 2009.
Janz et al., "Do idiopathic generalized epilepsies share a common susceptibility gene?" Neurology, vol. 42, Suppl 5, pp. 48-55 (Apr. 1992).
Kanai et al., "Effect of localization of missense mutations in SCN1A on epilepsy phenotype severity," Neurology, vol. 63, pp. 329-334 (2004).
Kimura K., "A missense mutation in SCN1A in brothers with severe myoclonic epilepsy in infancy (SMEI) inherited from a father with febrile seizures," Brain Dev., vol. 27, No. 6, pp. 424-430 (Sep. 2005).
Kinzler et al., "Identification of a gene located at chromosome 5q21 that is mutated in colorectal cancers," Science, vol. 251, pp. 1366-1370 (1991).
Kohler et al., "Continuous cultures of fused cells secreting antibody of predefined specificity," Nature, vol. 256, pp. 495-497 (1975).
Kozbor et al., "Specific immunoglobulin production and enhanced tumorigenicity following ascites growth of human hybridomas," Journal of Immunological Methods, vol. 81, pp. 31-42 (1985).
Lason W., "Neurochemical and pharmacological aspects of cocaine-induced seizures," Polish Journal of Pharmacology, vol. 53, pp. 57-60 (2001).
Lerche et al., "Ion Channels and Epilepsy," Am. J. of Med. Genetics, vol. 106, pp. 146-159 (2001).
Lernmark and Ott, "Sometimes it's hot, sometimes it's not," Nature Genetics, vol. 19, pp. 213-214 (Jul. 1998).
Lo et al., "High Level Expression and Secretion of Fc-X Fusion Proteins in Mammalian Cells," Protein Engineering, vol. 11, pp. 495-500 (1998).
Lopes-Cendes et al., "A New Locus for Generalized Epilepsy with Febrile Seizures Plus Maps to Chromosome 2," Am. J. Hum. Genet., vol. 66, pp. 698-701 (2000).
Lucentini, J., "Gene Asscoiation Studies Typically Wrong," The Scientist, p. 20 (Dec. 20, 2004).
Madia et al., "No evidence of GABRG2 mutations in severe myoclonic epilepsy of infancy," Epilepsy Research, vol. 53, pp. 196-200 (2003).
Malacarne et al., "Lack of SCN1A Mutations in Familial Febrile Seizures," Epelepsia, vol. 43, No. 5, pp. 559-562 (2002).
Maxam et al., "A new method for sequencing DNA," Proceedings of the National Academy of Sciences of the USA, vol. 74, No. 2, pp. 560-564 (1977).
Mazumder et al., "Translations control by the 3'•UTR: the ends specify the means," Trends in Biochemical Sciences, vol. 28, pp. 91-98 (2004).
Modrich, Paul, "Mechanisms and biological effects of mismatch repair," Annual Review of Genetics, vol. 25, pp. 229-253 (1991).
Moran et al., "Skeletal Muscle Sodium Channel Is Affected by an Epileptogenic β1 Subunit Mutation," Biochem. Biophys. Res. Comm., vol. 282, pp. 55-59 (2001).
Moulard et al., "Identification of a New Locus for Generalized Epilepsy wirh Febrile Seizures Plus (GEFS+) on Chromosome 2q24-q33," Am. J. Hum. Genet., vol. 65, pp. 1396-1400 (1999).
Mulley et al., "SCN1A Mutations and Epilepsy," Human Mutation, vol. 25, pp. 535-542 (2005).
Mulley et al., "Channelopathies as a Genetic Cause of Epilepsy," Current Opinion in Neurology, vol. 16, pp. 171-176 (2003).
N. Singh et al., "A novel potassium channel gene, KCNQ2, is mutated in an inherited epilepsy of newborns," Nature Genetics, vol. 18, pp. 25-29 (Jan. 1998).
Nabbout et al., "Spectrum of SCN1A Mutations in Severe Myoclonic Epilepsy of Infancy," Neurology, vol. 60, pp. 1961-1967 (Jun. 2003).
Notice of Allowance corresponding to U.S. Appl. No. 10/451,126 (Patent No. 7,078,515) dated Aug. 30, 2005.
Notice of Allowance corresponding to U.S. Appl. No. 11/263,326 dated Jun. 18, 2007.
Notice of Allowance corresponding to U.S. Appl. No. 11/262,647 dated Dec. 18, 2009.
Notice of Allowance corresponding to U.S. Appl. No. 10/806,899 dated Jan. 4, 2010.
Official Communication of U.S. Patent and Trademark Office corresponding to U.S. Appl. No. 10/482,834 dated Aug. 7, 2009.
Official Communication of U.S. Patent and Trademark Office corresponding to U.S. Appl. No. 10/482,834 dated Dec. 30, 2008.
Official Communication of U.S. Patent and Trademark Office corresponding to U.S. Appl. No. 10/482,834 dated Apr. 4, 2008.
Official Communication of U.S. Patent and Trademark Office corresponding to U.S. Appl. No. 10/482,834 dated Aug. 2, 2007.
Official Communication of U.S. Patent and Trademark Office corresponding to U.S. Appl. No. 10/806,899 dated Oct. 28, 2009.
Official Communication of U.S. Patent and Trademark Office corresponding to U.S. Appl. No. 10/806,899 dated May 13, 2009.
Official Communication of U.S. Patent and Trademark Office corresponding to U.S. Appl. No. 10/806,899 dated Aug. 19, 2008.
Official Communication of U.S. Patent and Trademark Office corresponding to U.S. Appl. No. 10/806,899 dated Jun. 26, 2007.
Official Communication of U.S. Patent and Trademark Office corresponding to U.S. Appl. No. 10/806,899 dated Nov. 29, 2006.
Official Communication of U.S. Patent and Trademark Office corresponding to U.S. Appl. No. 11/263,326 (Patent No. 7,282,336) dated Oct. 6, 2006.
Official Communication of U.S. Patent and Trademark Office corresponding to U.S. Appl. No. 11/262,647 dated Apr. 22, 2009.
Official Communication of U.S. Patent and Trademark Office corresponding to U.S. Appl. No. 11/262,647 dated Dec. 5, 2008.
Official Communication of U.S. Patent and Trademark Office corresponding to U.S. Appl. No. 11/262,647 dated Feb. 15, 2008.
Official Communication of U.S. Patent and Trademark Office corresponding to U.S. Appl. No. 10/451,126 (Patent No. 7,078,515) dated Jan. 24, 2005.
Ohmori et al., "Significant correlation of the SCN1A mutations and severe myoclonic epilepsy in infancy," Biochemical and Biophysical Research Communications, vol. 295, pp. 17-23 (2002).
Okubo et al., "Epileptiform EEG Discharges in Healthy Children: Prevalence, Emotional and Behavioral Correlates, and Genetic Influences," Epilepsia, vol. 35, No. 4, pp. 832-841 (1994).
Orita et al., "Detection of polymorphisms of human DNA by gel electrophoresis as single-strand confirmation polymorphisms," Proceedings of the National Academy of Sciences of the USA, vol. 86, pp. 2766-2770 (1989).
Orlandi et al., "Cloning immunoglobulin variable domains for expression by the polymerase chain reaction," Proceedings of the National Academy of Sciences of the USA, vol. 85, pp. 3833-3837 (1989).
Panayiotopoulos and Obeid, "Juvenile Myoclonic Epilepsy: An Autosomal Recessive Disease," Ann Neurol, vol. 25, pp. 440-443 (1989).
Peiffer et al., "A Locus of Febrile Seizures (FEB3) Maps to Chromosome 2q23-24," Annals of Neurology, vol. 46, No. 4, pp. 671-678 (Oct. 1999).
Phillips et al., "Autosomal Dominant Nocturnal Frontal-Lobe Epilepsy: Genetic Heterogeneity and Evidence for a Second Locus at 15q24," Am. J. Hum. Genet., vol. 63, pp. 1108-1116 (1998).
Phillips et al., "CHRNB2 is the Second Acetylcholine Receptor Sub-unit Associated with Autosomal Dominant Nocturnal Frontal Lobe Epilepsy," Am. J. Hum. Genet., vol. 68, pp. 225-231 (2001).
Phillips et al., "Localization of a gene for autosomal dominant nocturnal frontal lobe epilepsy to chromosome 20q13.2," Nature Genetics, vol. 10, pp. 117-118 (May 1995).
Plummer et al., "Evolution and Diversity of Mammalian Sodium Channel Genes," Genomics, vol. 57, pp. 323-331 (1999).
Reutens and Berkovic, "Idiopathic generalized epilepsy of adolescence: Are the syndromes clinically distinct?" Neurology, vol. 45, pp. 1469-1476 (Aug. 1995).
Rickert et al., "B lymphocyte-specific, Cre-mediated mutagenesis in mice," Nucleic Acids Research, vol. 25, No. 6, pp. 1317-1318 (1997).
Risch and Botstein, "A manic depressive history," Nature Genetics, vol. 12, pp. 351-353 (Apr. 1996).
Sanger et al., "DNA sequencing with chain-terminating inhibitors," Proceedings of the National Academy of Sciences of the USA, vol. 74, No. 12, pp. 5463-5467 (1977).

Scharf et al., "Heat stress promoters and transcription factors," Results and Problems in Cell Differentiation, vol. 20, pp. 125-162 (1994).

Scheffer and Berkovic, "Generalized epilepsy with febrile seizures plus A genetic disorder with heterogeneous clinical phenotypes," Brain, vol. 120, pp. 479-490 (1997).

Scheffer et al., "The Genetics of Human Epilepsy," TRENDS in Pharmacological Science, vol. 24, No. 8, pp. 428-433 (Aug. 2003).

Scheffer et al., "Locus for Febrile Seizures," Annals of Neurology, vol. 47, No. 6, pp. 840-841 (Jun. 2000).

Schena et al., "Parallel human genome analysis: Microarray-based expression monitoring of 1000 genes," Proceedings of the National Academy of Sciences of the USA, vol. 93, pp. 10614-10619 (1996).

Schwenk et al., "A cre-transgenic mouse strain for the ubiquitous deletion of loxP-flanked gene segments including deletion in germ cells," Nucleic Acids Research, vol. 23, No. 24, pp. 5080-5081 (1995).

Sheffield et al., "Attachment of a 40-base-pair G+C-rich sequence (GC-clamp) to genomic DNA fragments by the polymerase chain reaction results," Proceedings of the National Academy of Sciences of the USA, vol. 86, pp. 232-236 (1989).

Singh et al., "Severe Myoclonic Epilepsy of Infancy: Extended Spectrum of GEFS?" Epilepsia, vol. 42, No. 7, pp. 837-844 (2001).

Singh et al., "Generalized Epilepsy with Febrile Seizures Plus: A Common Childhood-Onset Genetic Epilepsy Syndrome," Ann. Neurol., vol. 45, pp. 75-81 (1999).

Spampanato et al., "Generalized Epilepsy with Febrile Seizures Plus Type 2 Mutation W1204R Alters voltage-Dependent Gating of $Na_v1.1$ Sodium Channels," Neuroscience, vol. 116, pp. 37-48 (2003).

Stafstrom et al., "Epilepsy Genes: The link between molecular dysfunction and pathophysiology", Mental Retardation and Developmental Disabilities Research Reviews, vol. 6, pp. 281-292 (2000).

Steinlein et al., "A missense mutation in the neuronal nicotinic acetylcholine receptor α4 subunit is associated with autosomal dominant nocturnal frontal lobe epilepsy," Nature Genetics, vol. 11, pp. 201-203 (Oct. 1995).

Sugawara et al., "Frequent mutations of SCN1A in severe myoclonic epilepsy in infancy," Neurology, vol. 58, pp. 1122-1124 (2002).

Sugawara, T., "Nav1.1 channels with mutations of severe myoclonic epilepsy in infancy display attenuated currents," Epilepsy Res., vol. 54, Nos. 2-3, pp. 201-207 (May 2003).

Supplementary European Search Report corresponding to Australian Patent No. AU0200910 dated Feb. 17, 2005.

Supplementary Partial European Search Report for Application No. 01271383.0-2406 dated Mar. 12, 2004.

Taylor et al., "Enzymatic methods for mutation scanning," Genetic Analysis: Biomolecular Engineering, vol. 14, pp. 181-186 (1999).

Thisted, "What is a P-value?" available online from www.stat.uchicago.edu, pp. 1-6 (May 25, 1998).

Todd, "Interpretation of results from genetic studies of multifactorial disease," Molecular Medicine, vol. 354, pp. 15-16 (Jul. 1999).

Veggiotti et al., "Generalized Epilepsy with Febrile Seizures plus and Severe Myoclonic Epilepsy in Infancy: a case report of two Italian families," Epileptic Discord, vol. 3, pp. 29-32 (2001).

Wallace et al., "Sodium Channel E L-Subunit Mutations in Severe Myoclonic Epilepsy of Infancy and Infantile Spasms," Neurology, vol. 61, pp. 765-769 (Sep. 2003).

Wallace et al., "Febrile seizures and generalized epilepsy associated with a mutation in the Na$^+$-channel β1 subunit gene SCN1B," Nature Genetics, vol. 19, pp. 366-370 (Aug. 1998).

Wallace et al., "Mutant $GABA_A$ receptor γ2-subunit in childhood absence epilepsy and febrile seizures," Nature Genetics, vol. 28, pp. 49-52 (May 2001).

Wallace et al., "Neuronal Sodium-Channel α1-Subunit Mutations in Generalized Epilepsy with Febrile Seizures Plus," The American Journal of Human Genetics, vol. 68, Issue 4, 859-865 (Apr. 1, 2001).

Wallace R., "A Plethora of SCN1A Mutations: What Can They Tell Us?" Epilepsy Curro., vol. 5, No. 1, pp. 17-20 (Jan. 2005).

Winter et al., "Man-made antibodies," Nature, vol. 349, pp. 293-299 (1991).

Wyman et al., "A highly polymorphic locus in human DNA," Proceedings of the National Academy of Sciences of the USA, vol. 77, No. 11, pp. 6754-6758 (1980).

Zara et al., "Mapping of genes predisposing to idiopathic generalized epilepsy," Human Molecular Genetics, vol. 4, No. 7, pp. 1201-1207 (1995).

Zara et al., "Mapping of Locus for a Familial Autosomal Recessive Idiopathic Myoclonic Epilepsy of Infancy to Chromosome 16p13," Am. J. Hum. Genet., vol. 66, pp. 1552-1557 (2000).

Abou-Khalil et al. Partial and generalized epilepsy with febrile seizures plus and a novel SCN1A mutation. Neurology, vol. 57, pp. 2265-2272 (2001).

Beaumanoir, In: Epileptic Syndromes in Infancy, Childhood and Adolescence, $2^{nd}$ ed., Roger J BM et al., editor, London: John Libbey & Co. Ltd., pp. 113-136 (2002).

Bendahhou et al., "Activation and Inactivation of the Voltage-Gated Sodium Channel: Role of Segment S5 Revealed by a Novel Hyperkalaemic Periodic Paralysis Mutation," J. Neurosci., vol. 19, pp. 4762-4771 (1999).

Blume, W. T., "Childhood brain tumors presenting as chronic uncontrolled focal seizure disorders," Ann. Neurol., vol. 4, pp. 541-547 (1978).

Blume et al., "Childhood Brain Tumors Presenting as Chronic Uncontrolled Focal Seizure Disorders," Annals of Neurology, vol. 12, No. 6, pp. 538-541 (Dec. 1982).

Burnstine et al., "Multifocal Independent epileptiform discharges in children: Ictal correlates and surgical therapy," Neurology, vol. 41, pp. 1223-1228 (1991).

Claes et al., "De novo SCN1A mutations are a major cause of severe myoclonic epilepsy of infancy," Hum. Mutat., vol. 21, pp. 615-621 (2003).

Doose et al., "Severe idiopathic generalized epilepsy of infancy with generalized tonic-clonic seizures," Neuropediatrics, vol. 29, pp. 229-238 (1998).

Dravet et al., In: Epileptic Syndromes in Infancy, Childhood and Adolescence, $3^{rd}$ ed., Eastleigh: John Libbey & Co., Ltd., pp. 81-103 (2002).

Fujiwara et al., "Long-Term Course of Childhood Epilepsy with Intractable Grand Mal Seizures," Jpn. J. Psychiatry Neurol., vol. 46, pp. 297-302 (1992).

Gamper et al., "Calmodulin mediates $Ca^{2+}$ dependent modulation of M-type $K^{30}$ channels", The Journal of General Physiology, vol. 122, pp. 17-31 (Jul. 2003).

Genbank accession No. AB093548, Oct. 16, 2001.

Genbank accession No. M22253, Oct. 26, 1995.

Genbank accession No. NM_012647, Mar. 21, 2010.

Genbank Accession No. NM_172107, Aug. 5, 2010.

Guerrini et al., Lamotrigine and seizure aggravation in severe myoclonic epilepsy, Epilepsia, vol. 39s, pp. 508-512 (1998).

International Preliminary Report on Patentability, corresponding to PCT application No. PCT/AU2004/00151 dated Feb. 23, 2006.

Italian League Against Epilepsy Genetic Collaborative Group, Epilepsia, vol. 34, pp. 819-826 (1993).

Jentsch, Thomas J., "Neuronal KCNQ potassium channels: physiology and role in disease", Neuroscience, Vo. 1, pp. 21-30 (Oct. 2000).

Kasai et al., "Genomic structures of SCN2A and SCN3A- candidate genes for deafness at the DFNA16 locus", Gene, vol. 264, pp. 113-122 (2001).

Kuhn et al., "Movement of voltage sensor S4 in domain 4 is tightly coupled to sodium channel fast inactivation and gating charge immobilization," J. Gen. Physiol., vol. 114, pp. 167-183 (1999).

Lu et al., "Isolation of a human-brain sodium-channel gene encoding two isoforms of the subtype III α-subunit," Journal of Molecular Neuroscience, vol. 10, pp. 67-70 (1998).

Malik et al., "Multifocal Independent Spike Syndrome (MISS): An Identifiable and Predictable Electroclinical Syndrome," Neurology, vol. 39, Suppl. 1, p. 189 (1989).

Markand, O. N., "Slow spike-wave activity in EEG and associated clinical features: often called 'Lennox' or 'Lennox-Gastaut' syndrome," Neurology, vol. 27, pp. 746-757 (1977).

Noda et al., "Existence of distinct sodium channel messenger RNAs in rat brain," Nature, vol. 320, pp. 188-192 (1986).

Noriega-Sanchez et al., "Clinical and electroencephalographic correlation of independent multifocal spike discharges," Neurology, vol. 26, pp. 667-672 (1976).

Office Action corresponding to U.S. Appl. No. 10/567,424 dated Feb. 11, 2011.

Office Action corresponding to U.S. Appl. No. 10/567,424 dated Oct. 13, 2010.

Ohmori et al., "Is phenotype difference in severe myoclonic epilepsy in infancy related to SCN1A mutations?," Brain Dev., vol. 25, pp. 488-493 (2003).

Ohtahara et al., "Lennox-Gastaut syndrome: a new vista," Psychiatry Clin. Neurosci., vol. 49, pp. S179-S183 (1995).

Ohtsuka et al., "Long-term prognosis of the Lennox-Gastaut syndrome," Jpn. J. Psychiatry Neurol., vol. 44, pp. 257-264 (1990).

Ohtsuka et al., "Refractory Childhood Epilepsy and Factors Related to Refractoriness," Epilepsia, vol. 41, Suppl. 9, pp. 14-17 (2000).

Ohya et al., "Diverse essential functions revealed by complementing yeast calmodulin mutants", Science, vol. 263, pp. 963-966 (Feb. 1994).

Palfi et al., "Differential calmodulin gene expression in the rodent brain", Life Sciences, vol. 70, pp. 2829-2855 (2002).

Roger et al., "Epileptic syndromes in infancy, childhood and adolescence", British Library Cataloguing in Publication Data, vol. 2, pp. 409-413 (1992).

Schmitt et al., "A recessive C-terminal Jervell and Lange-Nielsen mutation of the KCNQ1 channel impairs subunit assembly", The EMBO Journal, vol. 19, No. 3, pp. 332-340 (2000).

Schwake et al., "Surface expression and single channel properties of KCNQ2/KCNQ3, M-type K+ channels involved in epilepsy", The Journal of Biological Chemistry, vol. 275, No. 18, pp. 13343-13348 (2000).

Supplementary European Search Report corresponding to an EP application No. EP 04761088 dated May 18, 2007.

Toutenhoofd et al., "The calmodulin multigene family as a unique case of genetic redundancy: multiple levels of regulation to provide spatial and temporal control of calmodulin pools?" Cell Calcium, vol. 28, No. 2, pp. 83-96 (2000).

Wen et al., "Calmodulin is an auxiliary subunit of KCNQ2/3 potassium channels", The Journal of Neuroscience, vol. 22, No. 18, pp. 7991-8001 (Sep. 2002).

Yamatogi et al., "Severe Epilepsy with Multiple Independent Spike Foci," J. Clin. Neurophysiol., vol. 20, pp. 442-448 (2003).

Yus-Néjera et al., "The identification and characterization of a noncontinuous calmodulin-binding site in noninactivating voltage-dependent KCNQ potassium channels", The Journal of Biological Chemistry, vol. 277, No. 32, pp. 28545-28553 (2002).

* cited by examiner

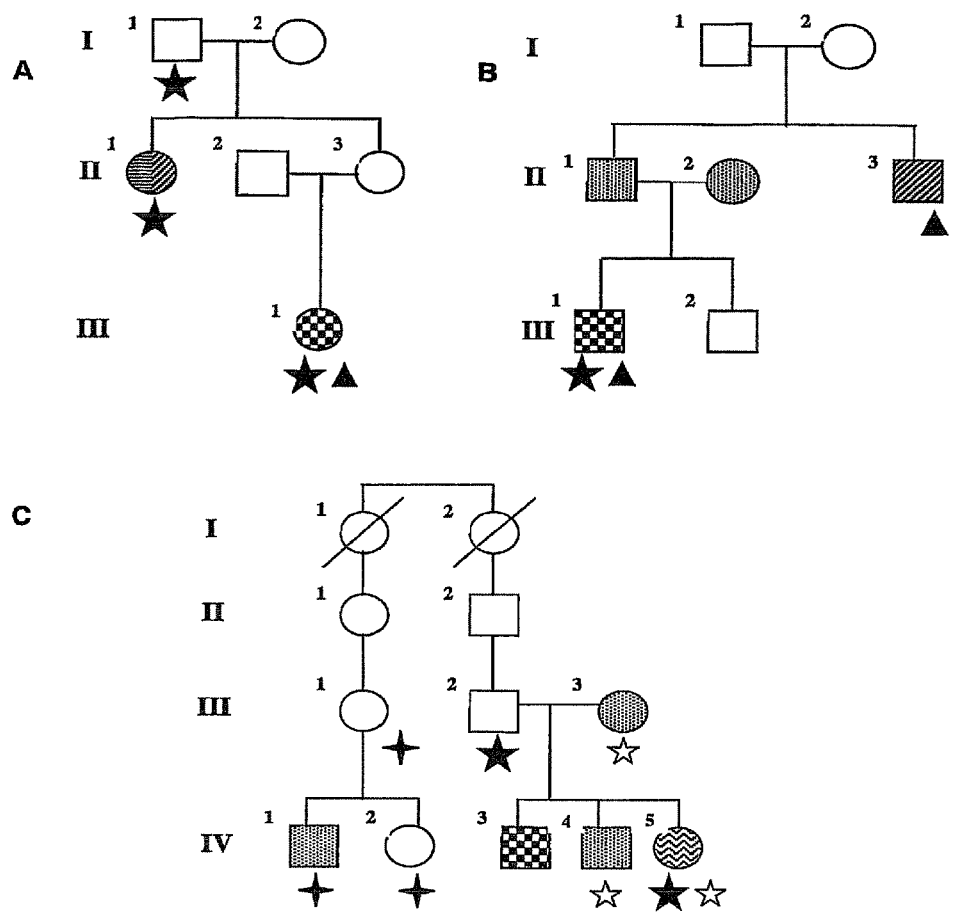

NUCLEIC ACID ENCODING SCN1A VARIANT

CROSS REFERENCE TO RELATED APPLICATIONS

This application is a divisional application of U.S. patent application Ser. No. 10/482,834, filed Oct. 12, 2004 now abandoned, which claims the benefit of PCT International Patent Application Serial No. PCT/AU02/00910, filed Jul. 8, 2002, which claims the benefit of Australian Provisional Patent Application Serial No. PS 2292, filed May 13, 2002, Australian Provisional Patent Application Serial No. PS 0910, filed Mar. 5, 2002, and Australian Provisional Patent Application Serial No. PR 6452, filed Jul. 18, 2001, the disclosure of each of which is incorporated herein by reference in their entirety.

TECHNICAL FIELD

The present invention is concerned with mutations in proteins having biological functions as ion channels and, more particularly, with such mutations where they are associated with diseases such as epilepsy and disorders associated with ion channel dysfunction including, but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness and total colour-blindness.

BACKGROUND ART

Epilepsies constitute a diverse collection of brain disorders that affect about 3% of the population at some time in their lives (Annegers, 1996). An epileptic seizure can be defined as an episodic change in behaviour caused by the disordered firing of populations of neurons in the central nervous system. This results in varying degrees of involuntary muscle contraction and often a loss of consciousness. Epilepsy syndromes have been classified into more than 40 distinct types based upon characteristic symptoms, types of seizure, cause, age of onset and EEG patterns (Commission on Classification and Terminology of the International League Against Epilepsy, 1989). However the single feature that is common to all syndromes is the persistent increase in neuronal excitability that is both occasionally and unpredictably expressed as a seizure.

A genetic contribution to the aetiology of epilepsy has been estimated to be present in approximately 40% of affected individuals (Gardiner, 2000). As epileptic seizures may be the end-point of a number of molecular aberrations that ultimately disturb neuronal synchrony, the genetic basis for epilepsy is likely to be heterogeneous. There are over 200 Mendelian diseases which include epilepsy as part of the phenotype. In these diseases, seizures are symptomatic of underlying neurological involvement such as disturbances in brain structure or function. In contrast, there are also a number of "pure" epilepsy syndromes in which epilepsy is the sole manifestation in the affected individuals. These are termed idiopathic and account for over 60% of all epilepsy cases.

Idiopathic epilepsies have been further divided into partial and generalized sub-types. Partial (focal or local) epileptic fits arise from localized cortical discharges, so that only certain groups of muscles are involved and consciousness may be retained (Sutton, 1990). However, in generalized epilepsy, EEG discharge shows no focus such that all subcortical regions of the brain are involved. Although the observation that generalized epilepsies are frequently inherited is understandable, the mechanism by which genetic defects, presumably expressed constitutively in the brain, give rise to partial seizures is less clear.

The molecular genetic era has resulted in spectacular advances in classification, diagnosis and biological understanding of numerous inherited neurological disorders including muscular dystrophies, familial neuropathies and spinocerebellar degenerations. These disorders are all uncommon or rare and have simple Mendelian inheritance. In contrast, common neurological diseases like epilepsy, have complex inheritance where they are determined by multiple genes sometimes interacting with environmental influences. Molecular genetic advances in disorders with complex inheritance have been far more modest to date (Todd, 1999).

Most of the molecular genetic advances have occurred by a sequential three stage process. First a clinically homogeneous disorder is identified and its mode of inheritance determined. Second, linkage analysis is performed on carefully characterized clinical populations with the disorder. Linkage analysis is a process where the chromosomal localization of a particular disorder is narrowed down to approximately 0.5% of the total genome. Knowledge of linkage imparts no intrinsic biological insights other than the important clue as to where to look in the genome for the abnormal gene. Third, strategies such as positional cloning or the positional candidate approach are used to identify the aberrant gene and its specific mutations within the linked region (Collins, 1995).

Linkage studies in disorders with complex inheritance have been bedeviled by negative results and by failure to replicate positive findings. A sense of frustration permeates current literature in the genetics of complex disorders. Carefully performed, large scale studies involving hundreds of sibpairs in disorders including multiple sclerosis and diabetes have been essentially negative (Bell and Lathrop, 1996; Lernmark and Ott, 1998). An emerging view is that such disorders are due to the summation of many genes of small effect and that identification of these genes may only be possible with very large-scale association studies. Such studies on a genome-wide basis are currently impossible due to incomplete marker sets and computational limitations.

The idiopathic generalized epilepsies (IGE) are the most common group of inherited human epilepsy and do not have simple inheritance. Like other complex disorders, linkage studies in IGE have generated controversial and conflicting claims. Previous authors have suggested the possibility of multifactorial, polygenic, oligogenic or two locus models for the disease (Andermann, 1982; Doose and Baier, 1989; Greenberg et al., 1988a; 1992; Janz et al., 1992).

Two broad groups of IGE are now known—the classical idiopathic generalized epilepsies (Commission on Classification and Terminology of the International League Against Epilepsy, 1989) and the newly recognized genetic syndrome of generalized epilepsy with febrile seizures plus (GEFS$^+$) (Scheffer and Berkovic, 1997; Singh et al., 1999).

The classical IGEs are divided into a number of clinically recognizable but overlapping sub-syndromes including childhood absence epilepsy, juvenile absence epilepsy, juvenile myoclonic epilepsy etc (Commission on Classification and Terminology of the International League Against Epilepsy, 1989; Roger et al., 1992). The sub-syndromes are identified by age of onset and the pattern of seizure types (absence, myoclonus and tonic-clonic). Some patients, particularly those with tonic-clonic seizures alone do not fit a specifically recognized sub-syndrome. Arguments for regarding these as separate syndromes, yet recognizing that they are part of a neurobiological continuum, have been presented previously (Berkovic et al. 1987; 1994; Reutens and Berkovic, 1995).

GEFS+ was originally recognized through large multi-generation families and comprises a variety of sub-syndromes. Febrile seizures plus (FS+) is a sub-syndrome where children have febrile seizures occurring outside the age range of 3 months to 6 years, or have associated febrile tonic-clonic seizures. Many family members have a phenotype indistinguishable from the classical febrile convulsion syndrome and some have FS+ with additional absence, myoclonic, atonic, or complex partial seizures. The severe end of the GEFS+ spectrum includes myoclonic-astatic epilepsy.

The cumulative incidence for epilepsy by age 30 years (proportion suffering from epilepsy at some time) is 1.5% (Hauser et al., 1993). Accurate estimates for the cumulative incidence of the IGEs are unavailable. In epidemiological studies where attempts are made to subclassify epilepsies, rather few cases of IGE are diagnosed, and many cases are unclassified. This is probably because cases are rarely directly examined by epileptologists. In clinic- or office-based series seen by experts, most cases are classifiable and IGEs account for about 25% of cases. This suggests that about 0.3% of the population suffer from IGE at some time.

In outbred populations many patients with classical IGE appear to be sporadic as siblings and parents are usually unaffected. Systematic EEG studies on clinically unaffected family members show an increase in age-dependent occurrence of generalized epileptiform discharges compared to controls. In addition, to the approximate 0.3% of the population with clinical IGE, systematic EEG studies suggest that about 1% of healthy children have generalized epileptiform discharges while awake (Cavazutti et al., 1980; Okubo et al., 1994).

Approximately 5-10% of first degree relatives of classical IGE probands have seizures with affected relatives usually having IGE phenotypes or febrile seizures. While nuclear families with 2-4 affected individuals are well recognized and 3 generation families or grandparent-grandchild pairs are occasionally observed (Italian League Against Epilepsy Genetic Collaborative Group, 1993), families with multiple affected individuals extending over 4 or more generations are exceptionally rare.

For GEFS+, however, a number of large multi-generation families showing autosomal dominant inheritance with incomplete penetrance are known. Similar to classical IGE, analysis of sporadic cases and small families with GEFS+ phenotypes does not suggest simple Mendelian inheritance. Indeed, bilineal inheritance, where there is a history of epilepsy on maternal and paternal sides, is observed in both GEFS+ and classical IGE families (Singh et al., 1999; Italian League Against Epilepsy Genetic Collaborative Group, 1993).

Within single families with classical IGE or GEFS+, affected individuals often have different sub-syndromes. The closer an affected relative is to the proband, the more similar are their sub-syndromes, and siblings often have similar sub-syndromes (Italian League Against Epilepsy Genetic Collaborative Group, 1993). Less commonly, families are observed where most, or all, known affected individuals have one classical IGE sub-syndrome such as childhood absence epilepsy or juvenile myoclonic epilepsy (Italian League Against Epilepsy Genetic Collaborative Group, 1993).

Importantly, sub-syndromes are identical in affected monozygous twins with IGE. In contrast, affected dizygous twins, may have the same or different sub-syndromes. Classical IGE and GEFS+ sub-syndromes tend to segregate separately (Singh et al., 1999).

In some inbred communities, pedigree analysis strongly suggests recessive inheritance for juvenile myoclonic epilepsy and other forms of IGE (Panayiotopoulos and Obeid, 1989; Berkovic et al., 2000). In such families, sub-syndromes are much more similar in affected siblings than in affected sib-pairs from outbred families. Recently, a family with an infantile form of IGE with autosomal recessive inheritance, confirmed by linkage analysis, was described in Italy (Zara et al., 2000).

Most work on the molecular genetics of classical IGEs has been done on the sub-syndrome of juvenile myoclonic epilepsy where a locus in proximity or within the HLA region on chromosome 6p was first reported in 1988 (Greenberg et al., 1988b). This finding was supported by two collaborating laboratories, in separate patient samples, and subsequently three groups provided further evidence for a 6p locus for juvenile myoclonic epilepsy in some, but not all, of their families. However, genetic defects have not been found and the exact locus of the gene or genes, in relationship to the HLA region, remains controversial. Strong evidence for linkage to chromosome 6 also comes from a study of a single large family with juvenile myoclonic epilepsy, but in this pedigree the locus is well outside the HLA region. A locus on chromosome 15q has also been suggested for juvenile myoclonic epilepsy, but was not confirmed by two other studies.

In general, the results of studies of the putative chromosomal 6p locus in the HLA region in patients with absence epilepsies or other forms of idiopathic generalized epilepsies have been negative. The major exception is that study of probands with tonic-clonic seizures on awakening, a sub-syndrome closely related to juvenile myoclonic epilepsy, suggests linkage to 6p.

Linkage for classical remitting childhood absence epilepsy remains elusive, but in a family with persisting absence evolving into a juvenile myoclonic epilepsy phenotype, linkage to chromosome 1p has been claimed. An Indian pedigree with persisting absence and tonic-clonic seizures may link to 8q24. Linkage to this region was also suggested by a non-parametric analysis in IGE, irrespective of subsyndrome, but was not confirmed in another study. Other loci for IGEs that have been reported in single studies include 3p14, 8p, 18 and possibly 5p. The unusual example of recessively inherited infantile onset IGE described in Italy maps to 16p in a single family.

Thus, like most disorders with complex inheritance, the literature on genetics of classical IGEs is confusing and contradictory. Some, and perhaps much, of this confusion is due to heterogeneity, with the likelihood of a number of loci for IGEs. The studies reviewed above were principally performed on multiple small families, so heterogeneity within and between samples is probable. Whether all, some, or none of the linkages reported above will be found to harbour relevant genes for IGE remains to be determined. Most of the studies reviewed above used analysis methods assuming Mendelian inheritance, an assumption that is not correct for outbred communities. Some studies used multiple models (autosomal recessive, autosomal dominant). Although parametric linkage analysis may be reliable in some circumstance of analyzing complex disease, it can lead to spurious findings as highlighted by the literature on linkage in major psychoses (Risch and Botstein, 1996).

In so far as GEFS+ is concerned, linkage analysis on rare multi-generation large families with clinical evidence of a major autosomal dominant gene have demonstrated loci on chromosomes 19q and 2q. Both the 19q and 2q GEFS+ loci have been confirmed in independently ascertained large families, and genetic defects have been identified. Families linked to 19q are known and a mutation in the gene for the β1 subunit of the neuronal sodium channel (SCN1B) has been identified (Wallace et al., 1998). This mutation results in the loss of a critical disulphide bridge of this regulatory subunit and causes a loss of function in vitro. Families linked to 2q are also known and mutations in the pore-forming α subunit of the neuronal sodium channel (SCN1A) have been identified (Australian provisional patent PR2203; Wallace et al., 2001b; Escayg et al., 2000). Studies on the more common small families with GEFS+ have not revealed these or other mutations to date.

In addition to the SCN1B and SCN1A mutations in GEFS+, four other gene defects have been discovered for human idiopathic epilepsies through the study of large families. Mutations in the alpha-4 subunit of the neuronal nicotinic acetylcholine receptor (CHRNA4) occur in the focal epilepsy syndrome of autosomal dominant nocturnal frontal lobe epilepsy (Australian patent AU-B-56247/96; Steinlein et al., 1995). Mutations in the gamma-2 subunit of the $GABA_A$ receptor (GABRG2) have been identified in childhood absence epilepsy, febrile seizures (including febrile seizures plus) and myoclonic epilepsy (PCT/AU01/00729; Wallace et al., 2001a). Finally, mutations in two potassium channel genes (KCNQ2 and KCNQ3) were identified in benign familial neonatal convulsions (Singh et al., 1998; Biervert et al., 1998; Charlier et al., 1998). Although initially regarded as a special form of IGE, this unusual syndrome is probably a form of inherited focal epilepsy.

Further to these studies, mutations in other genes have been identified to be causative of epilepsy. These include mutations in the beta-2 subunit (CHRNB2) of the neuronal nicotinic acetylcholine receptor (PCT/AU01/00541; Phillips et al., 2001) and the delta subunit (GABRD) of the $GABA_A$ receptor (PCT/AU01/00729).

A number of mouse models approximating human IGE are known. These mice mutants have ataxia in addition to generalized spike-and-wave discharges with absences or tonic-clonic seizures. Recessive mutations in calcium channel subunit genes have been found in lethargic (CACNB4), tottering/leaner (CACNA1A), and stargazer (CACNG2) mutants. The slow-wave epilepsy mouse mutant has a mutation in the sodium/hydrogen exchanger gene, which may have important downstream effects on pH-sensitive ion channels.

The human and mouse literature is now suggesting that the idiopathic epilepsies comprise a family of channelopathies with mutations in ion channel subunits of voltage-gated (eg SCN1A, SCN1B, KCNQ2, KCNQ3) or ligand-gated (eg CHRNA4, CHRNB2, GABRG2, GABRD) types. These channels are typically comprised of a number of subunits, specified by genes on different chromosomes. The stoichiometry and conformation of ion channel subunits are not yet well understood, but many have multiple subunits in a variety of combinations.

The involvement of ion channels in other neuro/physiological disorders has also been observed (reviewed in Dworakowska and Dolowy, 2000). Mutations in voltage-gated sodium, potassium, calcium and chloride channels as well as ligand-gated channels such as the acetylcholine and GABA receptors may lead to physiological disorders such as hyper- and hypo-kalemic periodic paralysis, myotonias, malignant hyperthermia, myasthenia and cardiac arrhythmias. Neurological disorders other than epilepsy that are associated with ion channel mutations include episodic ataxia, migraine, Alzheimer's disease, Parkinson's disease, schizophrenia, hyperekplexia, anxiety, depression, phobic obsessive symptoms, as well as neuropathic pain, inflammatory pain and chronic/acute pain. Some kidney disorders such as Bartter's syndrome, polycystic kidney disease and Dent's disease, secretion disorders such as hyperinsulinemic hypoglycemia of infancy and cystic fibrosis, and vision disorders such as congenital stationary night blindness and total colour-blindness may also be linked to mutations in ion channels.

DISCLOSURE OF THE INVENTION

In a new genetic model for the idiopathic generalised epilepsies (IGEs) described in PCT/AU01/00872 (the disclosure of which is incorporated herein by reference) it has been postulated that most classical IGE and GEFS+ cases are due to the combination of two mutations in multi-subunit ion channels. These are typically point mutations resulting in a subtle change of function. The critical postulate is that two mutations, usually, but not exclusively, in different subunit alleles ("digenic model"), are required for clinical expression of IGE. It was further proposed that a) A number of different mutated subunit pairs can be responsible for IGE. Combinations of two mutated subunits lead to an IGE genotype with ~30% penetrance.

b) The total allele frequency of mutated subunits is ~8%. It was calculated that approximately 15% of the population has one or more mutated subunit genes and 1% have two or more mutated subunits.

c) Sub-syndromes are principally determined by the specific combination of mutated subunit pairs, although one or more other genes, including ion channel subunits, of smaller effect may modify the phenotype.

d) Mutated subunit combinations that cause classical IGEs are largely separate from those that cause GEFS+, although some subunits may be involved in both syndromes.

e) Individuals with single 'change of function' mutations would not have IGE, but such mutations may contribute to simple febrile seizures, which are observed with increased frequency in relatives of IGE probands.

The model also proposes that subunit mutations with more severe functional consequences (eg breaking a disulphide bridge in SCN1B or amino acid substitution in the pore forming regions of SCN1A for GEFS+) cause autosomal dominant generalized epilepsies with a penetrance of 60-90%. The precise sub-syndromes in GEFS+ are determined by minor allelic variation or mutations in other ion channel subunits. Such "severe" mutations are rare (allele frequency <0.01%) and are infrequent causes of GEFS+. They very rarely, or perhaps never, cause classical IGE.

The identification of molecular changes in ion channel subunits is therefore a significant step towards the elucidation of genetic variants that alone or in combination (based on the digenic model) give rise to an epilepsy phenotype, and to other neuro/physiological disorders associated with ion channel dysfunction.

The present inventors have identified a number of novel mutations or variants in genes encoding subunits of ion channels in individuals with epilepsy. It will be appreciated that for each molecular defect one can provide an isolated nucleic acid molecule coding for a protein having a biological function as part of an ion channel in a mammal, wherein a mutation event selected from the group consisting of point mutations, deletions, insertions and rearrangements has occurred so as to affect the functioning of the ion channel. In some instances this single mutation alone will produce a phenotype of epilepsy or other neuro/physiological disorders associated with ion channel dysfunction.

In the case where a single mutation alone does not produce, say, an epilepsy phenotype, there would be provided one or more additional isolated nucleic acid molecules coding for proteins having a biological function as part of an ion channel in a mammal, wherein a mutation event selected from the group consisting of point mutations, deletions, insertions and rearrangements has occurred so as to affect the functioning of the ion channel. The cumulative effect of the mutations in each isolated nucleic acid molecule in vivo is to produce a epilepsy or another neuro/physiological disorders in said mammal. The mutations may be in nucleic acid molecules coding for protein subunits belonging to the same ion channel or may be in nucleic acid molecules coding for protein subunits that belong to different ion channels.

Typically such mutations are point mutations and the ion channels are voltage-gated channels such as a sodium, potassium, calcium or chloride channels or are ligand-gated channels such as members of the nAChR/GABA super family of receptors, or a functional fragment or homologue thereof.

Mutations may include those in non-coding regions of the ion channel subunits (eg mutations in the promoter region which affect the level of expression of the subunit gene, mutations in intronic sequences which affect the correct splicing of the subunit during mRNA processing, or mutations in the 5' or 3' untranslated regions that can affect translation or stability of the mRNA). Mutations may also and more preferably will be in coding regions of the ion channel subunits (eg nucleotide mutations may give rise to an amino acid change in the encoded protein or nucleotide mutations that do not give rise to an amino acid change but may affect the stability of the mRNA).

Mutation combinations may be selected from, but are not restricted to, those identified in Table 1.

Accordingly in one aspect of the present invention there is provided a method of identifying a subject predisposed to a disorder associated with ion channel dysfunction, comprising ascertaining whether at least one of the genes encoding ion channel subunits in said subject has undergone a mutation event such that a cDNA derived from said subject has the sequence set forth in one of SEQ ID NOS: 1-134.

In another aspect of the present invention there is provided an isolated nucleic acid molecule encoding a mutant or variant ion channel subunit wherein a mutation event has occurred such that a cDNA derived therefrom has the sequence set forth in one of SEQ ID NOS: 1-134.

The mutation event disrupts the functioning of an ion channel so as to produce a phenotype of epilepsy, and/or one or more other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness and total colour-blindness, either alone or in combination with one or more additional mutations or variations in the ion channel subunit genes.

In a further aspect of the present invention there is provided a combination of two or more isolated nucleic acid molecules each having a novel mutation event as laid out in Table 1. The cumulative effect of the mutations in each isolated nucleic acid molecule in vivo is to produce an epilepsy or another disorder associated with ion channel dysfunction as described above in said mammal.

In a particularly preferred embodiment of the present invention, the isolated nucleic acid molecules have a nucleotide sequence as shown in any one of SEQ ID Numbers: 1-134. The sequences correspond to the novel DNA mutations or variants laid out in Table 1.

In another aspect of the present invention there is provided an isolated nucleic acid molecule comprising any one of the nucleotide sequences set forth in SEQ ID NOS: 1-134.

In another aspect of the present invention there is provided an isolated nucleic acid molecule consisting of any one of the nucleotide sequences set forth in SEQ ID NOS: 1-134.

In another aspect of the present invention there is provided an isolated nucleic acid molecule encoding a mutant subunit of a mammalian nicotinic acetylcholine receptor (nAchR), wherein a mutation event selected from the group consisting of point mutations, deletions, insertions and rearrangements has occurred in the nucleotides outside of the M2 domain of the subunit of said mammalian nicotinic acetylcholine receptor, so as to produce an epilepsy phenotype.

Preferably said mutation event is a point mutation.

In one form of the invention, the mutations are in exon 5 of the CHRNA4 subunit and result in the replacement of an arginine residue with a cysteine residue at amino acid position 336, the replacement of an arginine residue with a glutamine residue at amino acid position 369, or the replacement of a proline residue with an arginine residue at amino acid position 474. The R336C mutation lies in the intracellular loop and occurs as a result of a C to T nucleotide substitution at position 1006 of the CHRNA4 coding sequence as shown in SEQ ID NO: 32. The R369Q mutation also lies in the intracellular loop and occurs as a result of a G to A nucleotide substitution at position 1106 of the CHRNA4 coding sequence as shown in SEQ ID NO: 33. Finally, the P474R lies in the intracellular loop and occurs as a result of a C to G nucleotide substitution at position 1421 of the CHRNA4 coding sequence as shown in SEQ ID NO: 34.

In a further form of the invention, the mutations are in exon 2 or 5 of the CHRNB2 subunit and result in the replacement of a threonine residue with a methionine residue at amino acid position 26, the replacement of a leucine residue with a valine residue at amino acid position 301, the replacement of a valine residue with an alanine residue at amino acid position 308, or the replacement of a glycine residue with an aspartic acid residue at amino acid position 412. The T26M mutation lies in the signal peptide and occurs as a result of a C to T nucleotide substitution at position 77 of the CHRNB2 coding sequence as shown in SEQ ID NO: 35. The L301V mutation lies in the M3 domain and occurs as a result of a C to G nucleotide substitution at position 901 of the CHRNB2 coding sequence as shown in SEQ ID NO: 36. The V308A mutation also lies in the M3 domain and occurs as a result of a T to C nucleotide substitution at position 923 of the CHRNB2 coding sequence as shown in SEQ ID NO: 134. Finally, the G412D mutation lies in the intracellular loop and occurs as a result of a G to A nucleotide substitution at position 1235 of the CHRNB2 coding sequence as shown in SEQ ID NO: 37.

Preferably these mutations create a phenotype of autosomal dominant nocturnal frontal lobe epilepsy.

The nucleotide sequences of the present invention can be engineered using methods accepted in the art for a variety of purposes. These include, but are not limited to, modification of the cloning, processing, and/or expression of the gene product. PCR reassembly of gene fragments and the use of synthetic oligonucleotides allow the engineering of the nucleotide sequences of the present invention. For example, oligonucleotide-mediated site-directed mutagenesis can introduce further mutations that create new restriction sites, alter expression patterns and produce splice variants etc.

As a result of the degeneracy of the genetic code, a number of polynucleotide sequences, some that may have minimal similarity to the polynucleotide sequences of any known and naturally occurring gene, may be produced. Thus, the invention includes each and every possible variation of a polynucleotide sequence that could be made by selecting combinations based on possible codon choices. These combinations are made in accordance with the standard triplet genetic code as applied to the polynucleotide sequences of the present invention, and all such variations are to be considered as being specifically disclosed.

The nucleic acid molecules of this invention are typically DNA molecules, and include cDNA, genomic DNA, synthetic forms, and mixed polymers, both sense and antisense strands, and may be chemically or biochemically modified, or may contain non-natural or derivatised nucleotide bases as will be appreciated by those skilled in the art. Such modifications include labels, methylation, intercalators, alkylators and modified linkages. In some instances it may be advantageous to produce nucleotide sequences possessing a substantially different codon usage than that of the polynucleotide sequences of the present invention. For example, codons may be selected to increase the rate of expression of the peptide in a particular prokaryotic or eukaryotic host corresponding with the frequency that particular codons are utilized by the host. Other reasons to alter the nucleotide sequence without altering the encoded amino acid sequences include the production of RNA transcripts having more desirable properties, such as a greater half-life, than transcripts produced from the naturally occurring mutated sequence.

The invention also encompasses production of DNA sequences of the present invention entirely by synthetic chemistry. Synthetic sequences may be inserted into expression vectors and cell systems that contain the necessary elements for transcriptional and translational control of the inserted coding sequence in a suitable host. These elements may include regulatory sequences, promoters, 5' and 3' untranslated regions and specific initiation signals (such as an ATG initiation codon and Kozak consensus sequence) which allow more efficient translation of sequences encoding the polypeptides of the present invention. In cases where the complete coding sequence, including the initiation codon and upstream regulatory sequences, are inserted into the appropriate expression vector, additional control signals may not be needed. However, in cases where only coding sequence, or a fragment thereof, is inserted, exogenous translational control signals as described above should be provided by the vector. Such signals may be of various origins, both natural and synthetic. The efficiency of expression may be enhanced by the inclusion of enhancers appropriate for the particular host cell system used (Scharf et al., 1994).

The invention also includes nucleic acid molecules that are the complements of the sequences described herein.

The present invention allows for the preparation of purified polypeptide or protein from the polynucleotides of the present invention, or variants thereof. In order to do this, host cells may be transformed with a novel DNA molecule as described above, or with DNA molecules encoding two or more mutant ion channel subunits. If the mutant subunits form a part of the same ion channel a receptor protein containing two or more mutant subunits may be isolated. If the mutant subunits are subunits of different ion channels the host cells will express two or more mutant receptor proteins. Typically said host cells are transfected with an expression vector comprising a DNA molecule according to the invention or, in particular, DNA molecules encoding two or more mutant ion channel subunits. A variety of expression vector/host systems may be utilized to contain and express sequences encoding polypeptides of the invention. These include, but are not limited to, microorganisms such as bacteria transformed with plasmid or cosmid DNA expression vectors; yeast transformed with yeast expression vectors; insect cell systems infected with viral expression vectors (e.g., baculovirus); or mouse or other animal or human tissue cell systems. Mammalian cells can also be used to express a protein using a vaccinia virus expression system. The invention is not limited by the host cell or vector employed.

The polynucleotide sequences, or variants thereof, of the present invention can be stably expressed in cell lines to allow long term production of recombinant proteins in mammalian systems. Sequences encoding the polypeptides of the present invention can be transformed into cell lines using expression vectors which may contain viral origins of replication and/or endogenous expression elements and a selectable marker gene on the same or on a separate vector. The selectable marker confers resistance to a selective agent, and its presence allows growth and recovery of cells which successfully express the introduced sequences. Resistant clones of stably transformed cells may be propagated using tissue culture techniques appropriate to the cell type.

The protein produced by a transformed cell may be secreted or retained intracellularly depending on the sequence and/or the vector used. As will be understood by those of skill in the art, expression vectors containing polynucleotides which encode a protein may be designed to contain signal sequences which direct secretion of the protein through a prokaryotic or eukaryotic cell membrane.

In addition, a host cell strain may be chosen for its ability to modulate is expression of the inserted sequences or to process the expressed protein in the desired fashion. Such modifications of the polypeptide include, but are not limited to, acetylation, glycosylation, phosphorylation, and acylation. Post-translational cleavage of a "prepro" form of the protein may also be used to specify protein targeting, folding, and/or activity. Different host cells having specific cellular machinery and characteristic mechanisms for post-translational activities (e.g., CHO or HeLa cells), are available from the American Type Culture Collection (ATCC) and may be chosen to ensure the correct modification and processing of the foreign protein.

When large quantities of the protein product of the gene are needed, such as for antibody production, vectors which direct high levels of expression of this protein may be used, such as those containing the T5 or T7 inducible bacteriophage promoter. The present invention also includes the use of the expression systems described above in generating and isolating fusion proteins which contain important functional domains of the protein. These fusion proteins are used for binding, structural and functional studies as well as for the generation of appropriate antibodies.

In order to express and purify the protein as a fusion protein, the appropriate cDNA sequence is inserted into a vector which contains a nucleotide sequence encoding another peptide (for example, glutathionine succinyl transferase). The fusion protein is expressed and recovered from prokaryotic or eukaryotic cells. The fusion protein can then be purified by affinity chromatography based upon the fusion vector sequence. The desired protein is then obtained by enzymatic cleavage of the fusion protein.

Fragments of the polypeptides of the present invention may also be produced by direct peptide synthesis using solidphase techniques. Automated synthesis may be achieved by using the ABI 431A Peptide Synthesizer (Perkin-Elmer). Various fragments of this protein may be synthesized separately and then combined to produce the full-length molecule.

The present invention is also concerned with polypeptides having a biological function as an ion channel in a mammal, wherein a mutation event selected from the group consisting of substitutions, deletions, truncations, insertions and rearrangements has occurred so as to affect the functioning of the ion channel. In some instances this single mutation alone will produce an epilepsy phenotype.

In the case where a single mutation alone does not produce an epilepsy phenotype, there would be provided one or more additional isolated mammalian polypeptides having biological functions as part of an ion channel in a mammal, wherein a mutation event selected from the group consisting of substitutions, deletions, truncations, insertions and rearrangements has occurred so as to affect the functioning of the ion channel. The cumulative effect of the mutations in each isolated mammalian polypeptide in vivo being to produce an epilepsy in said mammal. The mutations may be in polypeptide subunits belonging to the same ion channel as described above, but may also be in polypeptide subunits that belong to different ion channels.

Typically the mutation is an amino acid substitution and the ion channel is a voltage-gated channel such as a sodium, potassium, calcium or chloride channel or a ligand-gated channel such as a member of the nAChR/GABA super family of receptors, or a functional fragment or homologue thereof.

Mutation combinations may be selected from, but are not restricted to, those represented in Table 1.

Accordingly, in a further aspect of the present invention there is provided an isolated polypeptide, said polypeptide being a mutant or variant ion channel subunit wherein a mutation event has occurred such that the polypeptide has the amino acid sequence set forth in one of SEQ ID NOS: 135-173. The mutation event disrupts the functioning of an ion channel so as to produce a phenotype of epilepsy, and/or one or more other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness and total colour-blindness.

In a particularly preferred embodiment of the present invention, the isolated polypeptide has an amino acid sequence as shown in any one of SEQ ID Numbers: 135-173. The sequences correspond to the novel amino acid changes laid out in Table 1 for those instances where the DNA mutation results in an amino acid change.

In a still further aspect of the present invention there is provided a combination of two or more isolated polypeptides each having a novel mutation event as laid out in Table 1. The cumulative effect of the mutations in each isolated polypeptide molecule in vivo is to produce an epilepsy or another disorder associated with ion channel dysfunction as described above in said mammal.

In a particularly preferred embodiment of the present invention, the isolated polypeptides have an amino acid sequence as shown in any one of SEQ ID Numbers: 135-173. The sequences correspond to the novel amino acid changes laid out in Table 1.

According to still another aspect of the present invention there is provided an isolated polypeptide comprising the amino acid sequence set forth in any one of SEQ ID NOS: 135-173.

According to still another aspect of the present invention there is provided a polypeptide consisting of the amino acid sequence set forth in any one of SEQ ID NOS: 135-173.

According to still another aspect of the present invention there is provided an isolated polypeptide, said polypeptide being a mutant subunit of a mammalian nicotinic acetylcholine receptor (nAChR), wherein a mutation event selected from the group consisting of substitutions, deletions, insertions and rearrangements has occurred outside of the M2 domain, so as to produce an epilepsy phenotype.

In one form of the invention the mutations are located in the intracellular loop of the CHRNA4 subunit and are substitutions in which an arginine residue is replaced with a cysteine residue, an arginine residue is replaced with a glutamine, or a proline residue is replaced with an arginine. Preferably the substitutions are R336C, R369Q and P474R transitions as illustrated by SEQ ID NOS: 153, 154 and 155 respectively.

In a further form of the invention, the mutation event is a substitution in which a threonine residue is replaced with a methionine residue in the signal sequence of CHRNB2. Preferably the substitution is a T26M transition as illustrated in SEQ ID NO: 156.

In a still further form of the invention, the mutation events are substitutions in which a leucine residue is replaced with a valine residue, or a valine residue is replaced with an alanine located in the M3 domain of CHRNB2. Preferably the substitutions are a L301V or V308A transition as illustrated in SEQ ID NOS: 157 and 173.

In a still further form of the invention, the mutation event is a substitution in which a glycine residue is replaced with an aspartic acid residue located in the intracellular loop of CHRNB2. Preferably the substitution is a G412D transition as illustrated in SEQ ID NO: 158.

According to still another aspect of the present invention there is provided a method of preparing a polypeptide, comprising the steps of:

(1) culturing host cells transfected with an expression vector comprising a DNA molecule as described above under conditions effective for polypeptide production; and (2) harvesting the mutant ion channel subunit.

The mutant ion channel subunit may be allowed to assemble with other subunits constituting the channel that are either wild-type or themselves mutant subunits, whereby the assembled ion channel is harvested.

According to still another aspect of the invention there is provided a polypeptide which is the product of the process described above.

Substantially purified protein or fragments thereof can then be used in further biochemical analyses to establish secondary and tertiary structure. Such methodology is known in the art and includes, but is not restricted to, X-ray crystallography of crystals of the proteins or of the assembled ion channel incorporating the proteins or by nuclear magnetic resonance (NMR). Determination of structure allows for the rational design of pharmaceuticals to interact with the ion channel as a whole or through interaction with a specific subunit protein (see drug screening below), alter the overall ion channel protein charge configuration or charge interaction with other proteins, or to alter its function in the cell.

It will be appreciated that the mutant ion channel subunits included as part of the present invention will be useful in further applications which include a variety of hybridisation and immunological assays to screen for and detect the presence of either a normal or mutated gene or gene product. The invention enables therapeutic methods for the treatment of epilepsy as well as other disorders associated with ion channel dysfunction and also enables methods for the diagnosis of epilepsy as well as other disorders associated with ion channel dysfunction.

Therapeutic Applications

According to still another aspect of the invention there is provided a method of treating epilepsy as well as other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total colour-blindness, comprising administering a selective antagonist, agonist or modulator of an ion channel or ion channel subunit, when the ion channel contains a mutation in a subunit comprising the channel, as described above, to a subject in need of such treatment. Said mutation event may be causative of the disorder when expressed alone or when expressed in combination with one or more additional mutations in subunits of the same or different ion channels, which are typically those identified in Table 1.

In still another aspect of the invention there is provided the use of a selective antagonist, agonist or modulator of an ion channel or ion channel subunit when the ion channel contains a mutation in a subunit comprising the channel, as described above, said mutation being causative of epilepsy as well as other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total colour-blindness, when expressed alone or when expressed in combination with a second mutation in a subunit of the same or different ion channel, as described above, in the manufacture of a medicament for the treatment of the disorder.

In one aspect, a suitable antagonist, agonist or modulator will restore wild-type function to the ion channel or channels containing the mutations of the present invention, or will negate the effects the mutant channel or channels have on cell function.

Using methods well known in the art, a mutant ion channel may be used to produce antibodies specific for the mutant channel that is causative of the disease or to screen libraries of pharmaceutical agents to identify those that bind the mutant ion channel.

In one aspect, an antibody, which specifically binds to a mutant ion channel or mutant ion channel subunit of the invention, may be used directly as an agonist, antagonist or modulator, or indirectly as a targeting or delivery mechanism for bringing a pharmaceutical agent to cells or tissues that express the mutant ion channel.

In a still further aspect of the invention there is provided an antibody which is immunologically reactive with a polypeptide as described above, but not with a wild-type ion channel or ion channel subunit thereof.

In particular, there is provided an antibody to an assembled ion channel containing a mutation in a subunit comprising the receptor, which is causative of epilepsy or another disorder associated with ion channel dysfunction when expressed alone or when expressed in combination with one or more other mutations in subunits of the same or different ion channels. Such antibodies may include, but are not limited to, polyclonal, monoclonal, chimeric, and single chain antibodies as would be understood by the person skilled in the art.

For the production of antibodies, various hosts including rabbits, rats, goats, mice, humans, and others may be immunized by injection with a polypeptide as described above or with any fragment or oligopeptide thereof which has immunogenic properties. Various adjuvants may be used to increase immunological response and include, but are not limited to, Freund's, mineral gels such as aluminium hydroxide, and surface-active substances such as lysolecithin. Adjuvants used in humans include BCG (bacilli Calmette-Guerin) and *Corynebacterium parvum*.

It is preferred that the oligopeptides, peptides, or fragments used to induce antibodies to the mutant ion channel have an amino acid sequence consisting of at least 5 amino acids, and, more preferably, of at least 10 amino acids. It is also preferable that these oligopeptides, peptides, or fragments are identical to a portion of the amino acid sequence of the natural protein and contain the entire amino acid sequence of a small, naturally occurring molecule. Short stretches of ion channel amino acids may be fused with those of another protein, such as KLH, and antibodies to the chimeric molecule may be produced.

Monoclonal antibodies to a mutant ion channel may be prepared using any technique which provides for the production of antibody molecules by continuous cell lines in culture. These include, but are not limited to, the hybridoma technique, the human B-cell hybridoma technique, and the EBV-hybridoma technique. (For example, see Kohler et al., 1975; Kozbor et al., 1985; Cote et al., 1983; Cole et al., 1984).

Antibodies may also be produced by inducing in vivo production in the lymphocyte population or by screening immunoglobulin libraries or panels of highly specific binding reagents as disclosed in the literature. (For example, see Orlandi et al., 1989; Winter and Milstein, 1991).

Antibody fragments which contain specific binding sites for a mutant ion channel may also be generated. For example, such fragments include, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (For example, see Huse et al., 1989).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between an ion channel and its specific antibody. A two-site, monoclonal-based immunoassay utilizing antibodies reactive to two non-interfering ion channel epitopes is preferred, but a competitive binding assay may also be employed.

In a further aspect of the invention there is provided a method of treating epilepsy as well as other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total colour-blindness, comprising administering an isolated DNA molecule which is the complement (antisense) of any one of the DNA molecules described above and which encodes an RNA molecule that hybridizes with the mRNA encoding a mutant ion channel subunit of the invention, to a subject in need of such treatment.

Typically, a vector expressing the complement (antisense) of the polynucleotides of the invention may be administered to a subject in need of such treatment. Antisense strategies may use a variety of approaches including the use of antisense oligonucleotides, injection of antisense RNA, ribozymes, DNAzymes and transfection of antisense RNA expression vectors. Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (For example, see Goldman et al., 1997).

In a still further aspect of the invention there is provided the use of an isolated DNA molecule which is the complement (antisense) of a DNA molecule of the invention and which encodes an RNA molecule that hybridizes with the mRNA encoding a mutant ion channel subunit of the invention, in the manufacture of a medicament for the treatment of epilepsy as well as other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total colour-blindness.

In a further aspect, a suitable agonist, antagonist or modulator may include peptides, phosphopeptides or small organic or inorganic compounds that can restore wild-type activity of ion channels containing mutations in the subunits which comprise the channels as described above.

Peptides, phosphopeptides or small organic or inorganic compounds suitable for therapeutic applications may be identified using nucleic acids and peptides of the invention in drug screening applications as described below. Molecules identified from these screens may also be of therapeutic application in affected individuals carrying other ion channel subunit gene mutations if the molecule is able to correct the common underlying functional deficit imposed by these mutations and those of the invention.

There is therefore provided a method of treating epilepsy as well as other disorders associated with ion channel dysfunction comprising administering a compound that is a suitable agonist, antagonist or modulator of an ion channel and that has been identified using the mutant ion channel subunits of the invention.

In some instances, an appropriate approach for treatment may be combination therapy. This may involve the administering an antibody or complement (antisense) to a mutant ion channel or ion channel subunit of the invention to inhibit its functional effect, combined with administration of wild-type ion channel subunits which may restore levels of wild-type ion channel formation to normal levels. Wild-type ion channel subunits of the invention can be administered using gene therapy approaches as described above for complement administration.

There is therefore provided a method of treating epilepsy as well as other disorders associated with ion channel dysfunction comprising administration of an antibody or complement to a mutant ion channel or ion channel subunit of the invention in combination with administration of wild-type ion channel subunits.

In still another aspect of the invention there is provided the use of an antibody or complement to a mutant ion channel or ion channel subunit of the invention in combination with the use of wild-type ion channel subunits, in the manufacture of a medicament for the treatment of epilepsy as well as other disorders associated with ion channel dysfunction.

In further embodiments, any of the agonists, antagonists, modulators, antibodies, complementary sequences or vectors of the invention may be administered in combination with other appropriate therapeutic agents. Selection of the appropriate agents may be made by those skilled in the art, according to conventional pharmaceutical principles. The combination of therapeutic agents may act synergistically to effect the treatment or prevention of the various disorders described above. Using this approach, therapeutic efficacy with lower dosages of each agent may be possible, thus reducing the potential for adverse side effects.

Any of the therapeutic methods described above may be applied to any subject in need of such therapy, including, for example, mammals such as dogs, cats, cows, horses, rabbits, monkeys, and most preferably, humans.

Drug Screening

According to still another aspect of the invention, peptides of the invention, particularly purified mutant ion channel subunit polypeptide and cells expressing these, are useful for the screening of candidate pharmaceutical agents for the treatment of epilepsy as well as other as other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total colour-blindness.

Still further, it provides the use of a polypeptide complex for the screening of candidate pharmaceutical compounds.

Still further, it provides the use wherein high throughput screening techniques are employed.

Compounds that can be screened in accordance with the invention include, but are not limited to peptides (such as soluble peptides), phosphopeptides and small organic or inorganic molecules (such as natural product or synthetic chemical libraries and peptidomimetics).

In one embodiment, a screening assay may include a cell-based assay utilising eukaryotic or prokaryotic host cells that are stably transformed with recombinant molecules expressing the polypeptides or fragments of the invention, in competitive binding assays. Binding assays will measure the formation of complexes between a specific ion channel subunit polypeptide mutant or mutant fragment and the compound being tested, or will measure the degree to which a compound being tested will interfere with the formation of a complex between a specific ion channel subunit polypeptide mutant or mutant fragment and a known ligand.

The invention is particularly useful for screening compounds by using the polypeptides of the invention in transformed cells, transfected or injected oocytes, or animal models bearing mutated ion channel subunits such as transgenic animals or gene targeted (knock-in) animals (see transformed hosts). Drug candidates can be added to cultured cells that express a single mutant ion channel subunit or combination of mutant ion channel subunits (appropriate wild-type ion channel subunits should also be expressed for receptor assembly), can be added to oocytes transfected or injected with either a mutant ion channel subunit or combination of mutant ion channel subunits (appropriate wild-type ion channel subunits must also be injected for receptor assembly), or can be administered to an animal model containing a mutant ion channel or combination of mutant ion channels. Determining the ability of the test compound to modulate mutant ion channel activity can be accomplished by a number of techniques known in the art. These include for example measuring the effect on the current of the channel (e.g. calcium-, chloride-, sodium-, potassium-ion flux) as compared to the current of a cell or animal containing wild-type ion channels. Current in cells can be measured by a number of approaches including the patch-clamp technique (methods described in Hamill et al, 1981) or using fluorescence based assays as are known in the art (see Gonzalez et al. 1999). Drug candidates that alter the current to a more normal level are useful for treating or preventing epilepsy as well as other disorders associated with ion channel dysfunction.

Another technique for drug screening provides high-throughput screening for compounds having suitable binding affinity to the mutant ion channel subunit polypeptides of the invention or ion channels containing these (see PCT published application WO84/03564). In this stated technique, large numbers of small peptide test compounds can be synthesised on a solid substrate (such as a microtitre plate) and can be assayed for mutant ion channel subunit polypeptide or mutant ion channel binding. Bound mutant ion channel or mutant ion channel subunit polypeptide is then detected by methods well known in the art. In a variation of this technique, purified polypeptides of the invention can be coated directly onto plates to identify interacting test compounds.

The invention also contemplates the use of competition drug screening assays in which neutralizing antibodies capable of specifically binding the mutant ion channel compete with a test compound for binding thereto. In this manner, the antibodies can be used to detect the presence of any peptide that shares one or more antigenic determinants of the mutant ion channel.

The polypeptides of the present invention may also be used for screening compounds developed as a result of combinatorial library technology. This provides a way to test a large number of different substances for their ability to modulate activity of a polypeptide. A substance identified as a modulator of polypeptide function may be peptide or non-peptide in nature. Non-peptide "small molecules" are often preferred for many in vivo pharmaceutical applications. In addition, a mimic or mimetic of the substance may be designed for pharmaceutical use. The design of mimetics based on a known pharmaceutically active compound ("lead" compound) is a common approach to the development of novel pharmaceuticals. This is often desirable where the original active compound is difficult or expensive to synthesise or where it provides an unsuitable method of administration. In the design of a mimetic, particular parts of the original active compound that are important in determining the target property are identified. These parts or residues constituting the active region of the compound are known as its pharmacophore. Once found, the pharmacophore structure is modelled according to its physical properties using data from a range of sources including x-ray diffraction data and NMR. A template molecule is then selected onto which chemical groups which mimic the pharmacophore can be added. The selection can be made such that the mimetic is easy to synthesise, is likely to be pharmacologically acceptable, does not degrade in vivo and retains the biological activity of the lead compound. Further optimisation or modification can be carried out to select one or more final mimetics useful for in vivo or clinical testing.

It is also possible to isolate a target-specific antibody and then solve its crystal structure. In principle, this approach yields a pharmacophore upon which subsequent drug design can be based as described above. It may be possible to avoid protein crystallography altogether by generating anti-idiotypic antibodies (anti-ids) to a functional, pharmacologically active antibody. As a mirror image of a mirror image, the binding site of the anti-ids would be expected to be an analogue of the original receptor. The anti-id could then be used to isolate peptides from chemically or biologically produced peptide banks.

One superior method for drug screening relies on structure-based rational drug design. Determination of the three dimensional structure of the polypeptides of the invention, or the three dimensional structure of the ion channels which incorporate these polypeptides allows for structure-based drug design to identify biologically active lead compounds.

Three dimensional structural models can be generated by a number of applications, some of which include experimental models such as x-ray crystallography and NMR and/or from in silico studies of structural databases such as the Protein Databank (PDB). In addition, three dimensional structural models can be determined using a number of known protein structure prediction techniques based on the primary sequences of the polypeptides (e.g. SYBYL—Tripos Associated, St. Louis, Mo.), de novo protein structure design programs (e.g. MODELER—MSI Inc., San Diego, Calif., or MOE—Chemical Computing Group, Montreal, Canada) or ab initio methods (e.g. see U.S. Pat. Nos. 5,331,573 and 5,579,250).

Once the three dimensional structure of a polypeptide or polypeptide complex has been determined, structure-based drug discovery techniques can be employed to design biologically-active compounds based on these three dimensional structures. Such techniques are known in the art and include examples such as DOCK (University of California, San Francisco) or AUTODOCK (Scripps Research Institute, La Jolla, Calif.). A computational docking protocol will identify the active site or sites that are deemed important for protein activity based on a predicted protein model. Molecular databases, such as the Available Chemicals Directory (ACD) are then screened for molecules that complement the protein model.

Using methods such as these, potential clinical drug candidates can be identified and computationally ranked in order to reduce the time and expense associated with typical 'wet lab' drug screening methodologies.

Compounds identified through screening procedures as described above, and which are based on the use of the mutant nucleic acid and polypeptides of the invention, can also be tested for their effect on correcting the functional deficit imposed by other gene mutations in affected individuals including other ion channel subunit mutations.

Such compounds form a part of the present invention, as do pharmaceutical compositions containing these and a pharmaceutically acceptable carrier.

Pharmaceutical Preparations

Compounds identified from screening assays and shown to restore ion channel wild-type activity can be administered to a patient at a therapeutically effective dose to treat or ameliorate epilepsy as well as other disorders associated with ion channel dysfunction, as described above. A therapeutically effective dose refers to that amount of the compound sufficient to result in amelioration of symptoms of the disorder.

Toxicity and therapeutic efficacy of such compounds can be determined by standard pharmaceutical procedures in cell cultures or experimental animals. The data obtained from these studies can then be used in the formulation of a range of dosages for use in humans.

Pharmaceutical compositions for use in accordance with the present invention can be formulated in a conventional manner using one or more physiological acceptable carriers, excipients or stabilisers which are well known. Acceptable carriers, excipients or stabilizers are non-toxic at the dosages and concentrations employed, and include buffers such as phosphate, citrate, and other organic acids; antioxidants including absorbic acid; low molecular weight (less than about 10 residues) polypeptides; proteins, such as serum albumin, gelatin, or immunoglobulins; binding agents including hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or non-ionic surfactants such as Tween, Pluronics or polyethylene glycol (PEG).

The formulation of pharmaceutical compositions for use in accordance with the present invention will be based on the proposed route of administration. Routes of administration may include, but are not limited to, inhalation, insufflation (either through the mouth or nose), oral, buccal, rectal or parental administration.

Diagnostic Applications

Polynucleotide sequences encoding an ion channel subunit may be used for the diagnosis of epilepsy, as well as other as other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total colour-blindness, and the use of the DNA molecules incorporated as part of the invention in diagnosis of these disorders, or a predisposition to these disorders, is therefore contemplated. The DNA molecules incorporating the novel mutation events laid out in Table 1 may be used for this purpose.

The polynucleotides that may be used for diagnostic purposes include oligonucleotide sequences, genomic DNA and complementary RNA and DNA molecules. The polynucleotides may be used to detect and quantitate gene expression in biological samples. Genomic DNA used for the diagnosis may be obtained from body cells, such as those present in the blood, tissue biopsy, surgical specimen, or autopsy material. The DNA may be isolated and used directly for detection of a specific sequence or may be amplified by the polymerase chain reaction (PCR) prior to analysis. Similarly, RNA or cDNA may also be used, with or without PCR amplification. To detect a specific nucleic acid sequence, hybridisation using specific oligonucleotides, restriction enzyme digest and mapping, PCR mapping, RNAse protection, and various other methods may be employed. For instance direct nucleotide sequencing of amplification products from an ion channel subunit or subunits can be employed. Sequence of the sample amplicon is compared to that of the wild-type amplicon to determine the presence (or absence) of nucleotide differences.

According to a further aspect of the invention there is provided the use of a polypeptide as described above in the diagnosis of epilepsy as well as other as other disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total colour-blindness.

When a diagnostic assay is to be based upon proteins constituting an ion channel, a variety of approaches are possible. For example, diagnosis can be achieved by monitoring differences in the electrophoretic mobility of normal and mutant proteins that form the ion channel. Such an approach will be particularly useful in identifying mutants in which charge substitutions are present, or in which insertions, deletions or substitutions have resulted in a significant change in the electrophoretic migration of the resultant protein. Alternatively, diagnosis may be based upon differences in the proteolytic cleavage patterns of normal and mutant proteins, differences in molar ratios of the various amino acid residues, or by functional assays demonstrating altered function of the gene products.

In another aspect, antibodies that specifically bind mutant ion channels may be used for the diagnosis of a disorder, or in assays to monitor patients being treated with a complete ion channel or agonists, antagonists, modulators or inhibitors of an ion channel. Antibodies useful for diagnostic purposes may be prepared in the same manner as described above for therapeutics. Diagnostic assays for ion channels include methods that utilize the antibody and a label to detect a mutant ion channel in human body fluids or in extracts of cells or tissues. The antibodies may be used with or without modification, and may be labelled by covalent or non-covalent attachment of a reporter molecule.

A variety of protocols for measuring the presence of mutant ion channels, including but not restricted to, ELISAs, RIAs, and FACS, are known in the art and provide a basis for diagnosing a disorder. The expression of a mutant ion channel or combination of mutant ion channels is established by combining body fluids or cell extracts taken from test mammalian subjects, preferably human, with antibody to the ion channel or channels under conditions suitable for complex formation. The amount of complex formation may be quantitated by various methods, preferably by photometric means. Antibodies specific for the mutant ion channels will only bind to individuals expressing the said mutant ion channels and not to individuals expressing only wild-type channels (ie normal individuals). This establishes the basis for diagnosing the disorder.

Once an individual has been diagnosed with a disorder, effective treatments can be initiated as described above. Treatments can be directed to amend the combination of ion channel subunit mutations or may be directed to one mutation.

Microarray

In further embodiments, complete cDNAs, oligonucleotides or longer fragments derived from any of the polynucleotide sequences described herein may be used as probes in a microarray. The microarray can be used to diagnose epilepsy, as well as other disorders associated with ion channel dysfunction, through the identification of genetic variants, mutations, and polymorphisms in the ion channel subunits that form part of the invention, to understand the genetic basis of a disorder, or can be used to develop and monitor the activities of therapeutic agents.

According to a further aspect of the present invention, tissue material obtained from animal models generated as a result of the identification of specific ion channel subunit human mutations (see below), particularly those disclosed in the present invention, can be used in microarray experiments. These experiments can be conducted to identify the level of expression of specific ion channel subunits, or any cDNA clones from whole-tissue libraries, in diseased tissue as opposed to normal control tissue. Variations in the expression level of genes, including ion channel subunits, between the two tissues indicates their possible involvement in the disease process either as a cause or consequence of the original ion channel subunit mutation present in the animal model. These experiments may be used to determine gene function, to understand the genetic basis of a disorder, to diagnose a disorder, and to develop and monitor the activities of therapeutic agents. Microarrays may be prepared, used, and analyzed using methods known in the art. (For example, see Schena et al., 1996; Heller et al., 1997).

Transformed Hosts

The present invention also provides for the production of genetically modified (knock-out, knock-in and transgenic), non-human animal models transformed with nucleic acid molecules containing the novel ion channel mutations or variants as laid out in Table 1. These animals are useful for the study of the function of ion channels, to study the mechanisms by which combinations of mutations in ion channel subunits interact to give rise to disease and the effects of these mutations on tissue development, for the screening of candidate pharmaceutical compounds, for the creation of explanted mammalian cell cultures which express mutant ion channels or combinations of mutant ion channels, and for the evaluation of potential therapeutic interventions.

Animal species which are suitable for use in the animal models of the present invention include, but are not limited to, rats, mice, hamsters, guinea pigs, rabbits, dogs, cats, goats, sheep, pigs, and non-human primates such as monkeys and chimpanzees. For initial studies, genetically modified mice and rats are highly desirable due to the relative ease in generating knock-in, knock-out or transgenics of these animals, their ease of maintenance and their shorter life spans. For certain studies, transgenic yeast or invertebrates may be suitable and preferred because they allow for rapid screening and provide for much easier handling. For longer term studies, non-human primates may be desired due to their similarity with humans.

To create an animal model for a mutated ion channel, or an animal model incorporating a combination of mutations, several methods can be employed. These include but are not limited to generation of a specific mutation in a homologous animal gene, insertion of a wild type human gene and/or a humanized animal gene by homologous recombination, insertion of a mutant (single or multiple) human gene as genomic or minigene cDNA constructs using wild type or mutant or artificial promoter elements or insertion of artificially modified fragments of the endogenous gene by homologous recombination. The modifications include insertion of mutant stop codons, the deletion of DNA sequences, or the inclusion of recombination elements (lox p sites) recognized by enzymes such as Cre recombinase.

To create transgenic or gene targeted (knock-in) mice, which are preferred, a mutant version of a particular ion channel subunit or combination of subunits can be inserted into a mouse germ line using standard techniques of oocyte microinjection. Alternatively, if it is desired to inactivate or replace an endogenous ion channel subunit gene, homologous recombination using embryonic stem cells may be applied.

For oocyte injection, one or more copies of the mutant ion channel subunit gene, or combinations thereof, can be inserted into the pronucleus of a just-fertilized mouse oocyte. This oocyte is then reimplanted into a pseudo-pregnant foster mother. The liveborn mice can then be screened for integrants using analysis of tail DNA or DNA from other tissues for the presence of the particular human subunit gene sequence. The transgene can be either a complete genomic sequence injected as a YAC, BAC, PAC or other chromosome DNA fragment, a complete cDNA with either the natural promoter or a heterologous promoter, or a minigene containing all of the coding region and other elements found to be necessary for optimum expression.

Once animals have been produced which contain a specific mutation in a particular ion channel subunit, mating combinations may be initiated between such animals so as to produce progeny containing combinations of two or more ion channel mutations. These animals effectively mimic combinations of mutations that are proposed here to cause human IGE cases. These animal models can subsequently be used to study the extent and mechanisms of disease as related to the mutated ion channel combinations, as well as for the screening of candidate therapeutic compounds.

According to still another aspect of the invention there is provided the use of genetically modified non-human animals as described above for the screening of candidate pharmaceutical compounds (see drug screening above). These animals are also useful for the evaluation (eg therapeutic efficacy, toxicity, metabolism) of candidate pharmaceutical compounds, including those identified from the invention as described above, for the treatment of epilepsy as well as other as other disorders associated with ion channel dysfunction as described above.

It will be clearly understood that, although a number of prior art publications are referred to herein, this reference does not constitute an admission that any of these documents forms part of the common general knowledge in the art, in Australia or in any other country.

Throughout this specification and the claims, the words "comprise", "comprises" and "comprising" are used in a non-exclusive sense, except where the context requires otherwise.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

BRIEF DESCRIPTION OF THE DRAWINGS

Preferred forms of the invention will now be described, by way of example only, with reference to the following examples and the accompanying drawings, in which:

FIG. 1A: A typical channel may have five subunits of three different types. FIG. 1B: In outbred populations complex diseases such as idiopathic generalized epilepsies may be due to mutations in two (or more) different subunit genes. Because only one allele of each subunit gene is abnormal, half the expressed subunits will have the mutation. FIG. 1C: In inbred populations, both alleles of a single subunit gene will be affected, so all expressed subunits will be mutated. FIG. 1D: Autosomal dominant disorders can be attributed to single ion channel subunit mutations that give rise to severe functional consequences;

FIG. 3 provides examples of epilepsy pedigrees where mutation profiles of ion channel subunits for individuals constituting the pedigree have begun to be determined. These examples have been used to illustrate how the identification of novel ion channel subunit mutations and variations in IGE individuals can combine to give rise to the disorder.

MODES FOR PERFORMING THE INVENTION

Figure 1:
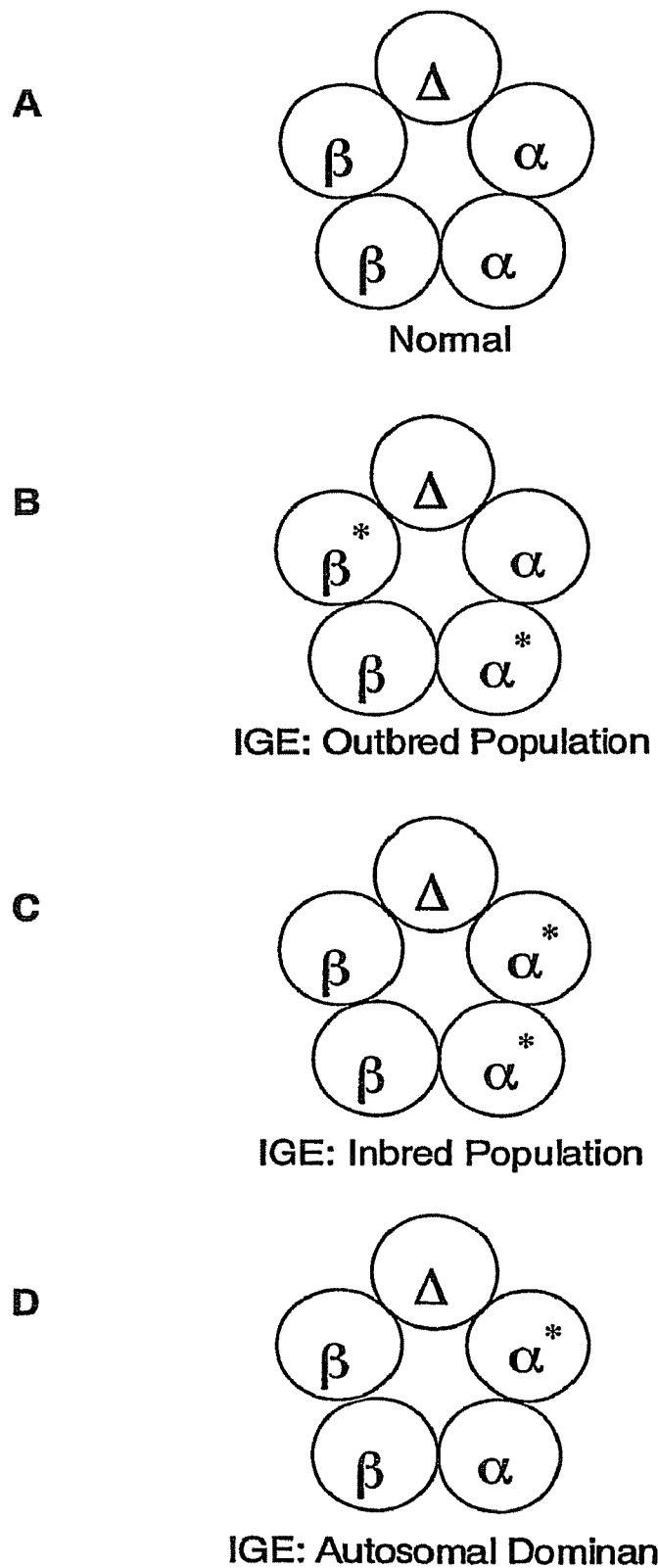
FIG. 1 provides an example of ion channel subunit stoichiometry and the effect of multiple versus single ion channel subunit mutations.

Potassium channels are the most diverse class of ion channel. The *C. elegans* genome encodes about 80 different potassium channel genes and there are probably more in mammals. About ten potassium channel genes are known to be mutated in human disease and include four members of the KCNQ gene sub-family of potassium channels. KCNQ proteins have six transmembrane domains, a single P-loop that forms the selectivity filter of the pore, a positively charged fourth transmembrane domain that probably acts as a voltage sensor and intracellular amino and carboxy termini. The C terminus is long and contains a conserved "A domain" followed by a short stretch thought to be involved in subunit assembly.

Four KCNQ subunits are thought to combine to form a functional potassium channel. All five known KCNQ proteins can form homomeric channels in vitro and the formation of heteromers appears to be restricted to certain combinations.

Sodium (the alpha subunit) and calcium channels are thought to have evolved from the potassium channel subunit, and they each consist of four domains covalently linked as the one molecule, each domain being equivalent to one of the subunits that associate to form the potassium channel. Each of the four domains of the sodium and calcium channels are comprised of six transmembrane segments.

Voltage-gated sodium channels are required to generate the electrical excitation in neurones, heart and skeletal muscle fibres, which express tissue specific isoforms. Sodium channels are heteromers of a pore forming alpha subunit and a modulatory beta-1 subunit, with an additional beta-2 subunit in neuronal channels. Ten genes encoding sodium channel alpha subunits and 3 genes encoding different beta subunits have so far been identified. The beta subunits of the sodium channels do not associate with the alpha subunits to form any part of the pore, they do however affect the way the alpha pore forming subunit functions.

As with sodium channels, calcium channels consist of a single pore forming alpha subunit, of which at least six types have been identified to date, and several accessory subunits including four beta, one gamma and one alpha2-delta gene. Many of these subunits also encode multiple splice variants adding to the diversity of receptor subunits of this family of ion channels.

The ion channels in the nAChR/GABA super family show a theoretical pentameric channel. Gamma-Aminobutyric acid (GABA) is the most abundant inhibitory neurotransmitter in the central nervous system. GABA-ergic inhibition is mediated by two major classes of receptors, type A (GABA-A) and type B (GABA-B). GABA-B receptors are members of the class of receptors coupled to G-proteins and mediate a variety of inhibitory effects via secondary messenger cascades. GABA-A receptors are ligand-gated chloride channels that mediate rapid inhibition.

The GABA-A channel has 16 separate, but related, genes encoding subunits. These are grouped on the basis of sequence identity into alpha, beta, gamma, delta, epsilon, theta and pi subunits. There are six alpha subunits ($\alpha$1-$\alpha$6), three beta subunits ($\beta$1-$\beta$3) and three gamma subunits ($\gamma$1-$\gamma$3). Each GABA-A receptor comprises five subunits which may, at least in theory, be selected from any of these subunits.

Neuronal nicotinic acetylcholine receptors (nAChRs) consist of heterologous pentamers comprising various combinations of alpha subunits or alpha and beta subunits ($\alpha$2-$\alpha$9; $\beta$2-$\beta$4). The alpha subunits are characterised by adjacent cysteine residues at amino acid positions 192 and 193, and the beta subunits by the lack of these cysteine residues. They are ligand-gated ion channels differentially expressed throughout the brain to form physiologically and pharmacologically distinct receptors hypothesised to mediate fast, excitatory transmission between neurons of the central nervous system or to modulate neurotransmission from their presynaptic position.

In chicken and rat, the predominant nAChR subtype is composed of alpha-4 and beta-2 subunits. The transmembrane 2 (M2) segments of the subunits are arranged as alpha helices and contribute to the walls of the neurotransmitter-gated ion channel. The alpha helices appear to be kinked and orientated in such a way that the side chains of the highly conserved M2-leucine residues project inwards when the channel is closed. ACh is thought to cause a conformational change by altering the association of the amino acid residues of M2. The opening of the channel seems to be due to rotations of the gate forming side chains of the amino acid residues; the conserved polar serines and threonines may form the critical gate in the open channel.

Disclosed is an isolated polypeptide, the polypeptide being a mutant or variant ion channel subunit wherein a mutation event has occurred such that the polypeptide has the amino acid sequence set forth in one of SEQ ID NOS: 135-173. The mutation event can disrupt the functioning of an assembled ion channel so as to produce an epilepsy phenotype. The mutation event can disrupt the functioning of an assembled ion channel so as to produce one or more disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness and total color-blindness.

The mutation event can disrupt the functioning of an assembled ion channel so as to produce an epilepsy phenotype when expressed in combination with one or more additional mutations or variations in said ion channel subunit genes. The mutation event can disrupts the functioning of an assembled ion channel so as to produce one or more disorders associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness and total color-blindness, when expressed in combination with one or more additional mutations or variations in the ion channel subunit genes.

Also disclosed is an isolated polypeptide comprising any one of the amino acid sequences set forth in SEQ ID NOS: 135-173. Also disclosed is an isolated polypeptide consisting of any one of the amino acid sequences set forth in SEQ ID NOS: 135-173. Also disclosed is an isolated polypeptide complex, the polypeptide complex being an assembled mammalian ion channel including an ion channel subunit comprising a polypeptide as defined herein.

An antibody, which is immunologically reactive with an isolated polypeptide as defined herein, or an isolated polypeptide complex as defined herein, is also disclosed. The antibody can be selected from the group consisting of a monoclonal antibody, a humanised antibody, a chimeric antibody or an antibody fragment including a Fab fragment, (Fab')2 fragment, Fv fragment, single chain antibodies and single domain antibodies. Also disclosed is a method of treating epilepsy comprising administering an antibody as disclosed herein to a subject in need of such treatment. Also disclosed is the use of an antibody, as disclosed herein, in the manufacture of a medicament for the treatment of epilepsy.

Also disclosed is a method of treating a disorder associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total color-blindness, comprising administering an antibody as disclosed herein to a subject in need of such treatment. Also disclosed is the use of an antibody, as defined herein, in the manufacture of a medicament for the treatment of a disorder associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total color-blindness.

A method of treating epilepsy comprising administering a selective agonist, antagonist or modulator of an ion channel when it has undergone a mutation event or combination of events as defined herein to a subject in need of such treatment is disclosed, as is the use of a selective agonist, antagonist or modulator of an ion channel when it has undergone a mutation event as herein in the manufacture of a medicament for the treatment of epilepsy.

A method of treating a disorder associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total color-blindness is disclosed. The method can comprise administering a selective agonist, antagonist or modulator of an ion channel when it has undergone a mutation event or combination of events as defined herein to a subject in need of such treatment.

Also disclosed is the use of a selective agonist, antagonist or modulator of an ion channel when it has undergone a mutation event as defined herein in the manufacture of a medicament for the treatment of a disorder associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total color-blindness.

A method of treating epilepsy is disclosed, the method comprising administering an isolated DNA molecule which is the complement (antisense) of a nucleic acid molecule as defined herein and which encodes an RNA molecule that hybridizes with the mRNA encoded by a nucleic acid molecule as defined herein, to a subject in need of such treatment. The use of a DNA molecule which is the complement of a nucleic acid molecule as defined herein and which encodes an RNA molecule that hybridizes with the mRNA encoded by a nucleic acid molecule defined herein, in the manufacture of a medicament for the treatment of epilepsy is also disclosed.

A method of treating a disorder associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total color-blindness, is disclosed. The method can comprise administering an isolated DNA molecule which is the complement (antisense) of a nucleic acid molecule as defined herein and which encodes an RNA molecule that hybridizes with the mRNA encoded by a nucleic acid molecule as defined herein, to a subject in need of such treatment.

Also disclosed is the use of a DNA molecule which is the complement of a nucleic acid molecule as defined herein and which encodes an RNA molecule that hybridizes with the mRNA encoded by a nucleic acid molecule as defined herein, in the manufacture of a medicament for the treatment of a disorder associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total color-blindness.

A method of treating epilepsy is disclosed, the method comprising administering an antibody, as defined herein, administration of an agonist, antagonist or modulator of an ion channel when it has undergone a mutation event or combination of events as defined herein, or administration of a DNA molecule which is the complement of a nucleic acid molecule defined herein and which encodes an RNA molecule that hybridizes with the mRNA encoded by a nucleic acid molecule as defined herein, in combination with administration of the wild-type ion channel subunit, to a subject in need of such treatment.

The use of an antibody, as defined herein, use of an agonist, antagonist or modulator of an ion channel when it has undergone a mutation event or combination of events as defined herein, or use of a DNA molecule which is the complement of a nucleic acid molecule as defined herein and which encodes an RNA molecule that hybridizes with the mRNA encoded by a nucleic acid molecule as defined herein, in combination with the use of the wild-type ion channel subunit, in the manufacture of a medicament for the treatment of epilepsy, is also disclosed.

A method of treating a disorder associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total color-blindness is also disclosed. The method can comprise administering an antibody, as defined herein, administration of an agonist, antagonist or modulator of an ion channel when it has undergone a mutation event or combination of events as defined herein, or administration of a DNA molecule which is the complement of a nucleic acid molecule as defined herein and which encodes an RNA molecule that hybridizes with the mRNA encoded by a nucleic acid molecule as defined herein, in combination with administration of the wild-type ion channel subunit, to a subject in need of such treatment.

Also disclosed is the use of an antibody, as defined herein, use of an agonist, antagonist or modulator of an ion channel when it has undergone a mutation event or combination of events as defined herein, or use of a DNA molecule which is the complement of a nucleic acid molecule as defined herein and which encodes an RNA molecule that hybridizes with the mRNA encoded by a nucleic acid molecule as defined herein, in combination with the use of the wild-type ion channel subunit, in the manufacture of a medicament for the treatment of a disorder associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total color-blindness.

Also disclosed is the use of an antibody as defined herein in the diagnosis of epilepsy and in the diagnosis of a disorder associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total color-blindness.

Also disclosed is a method of producing a non-human transgenic animal containing a combination of two or more ion channel mutations, comprising the steps of: creating a non-human transgenic animal comprising a first nucleic acid molecule as defined herein; creating one or more additional non-human, transgenic animals comprising a second nucleic acid molecule as defined herein; and conducting mating combinations so as to produce progeny containing combinations of two or more ion channel mutations which effectively mimic combinations of ion channel mutations responsible for human disease. A non-human, transgenic animal produced by the process is also disclosed.

Also disclosed is an isolated polypeptide, the polypeptide being a mutant subunit of a mammalian nicotinic acetylcholine receptor (nAChR), wherein a mutation event selected from the group consisting of substitutions, deletions, insertions and rearrangements has occurred outside of the M2 domain, so as to produce an epilepsy phenotype.

Also disclosed is an isolated polypeptide, the polypeptide being a mutant subunit of a mammalian nicotinic acetylcholine receptor (nAChR), wherein a mutation event selected from the group consisting of substitutions, deletions, insertions and rearrangements has occurred outside of the M2 domain, so as to produce a disorder associated with ion channel dysfunction, including but not restricted to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness or total color-blindness. For the foregoing isolated polypeptides, the mutant subunit can be the CHRNA4 subunit. The mutation event can take place in the intracellular loop of the CHRNA4 subunit. The mutation event can be selected from the group consisting of an R336C mutation, R369Q mutation and P474R mutation. The mutant subunit can be the CHRNB2 subunit. The mutation event can take place in the signal sequence. The mutation event can be a T26M substitution. The mutation event can take place in the M3 domain. The mutation event can be an L301V substitution or a V308A substitution. The mutation event can take place in the intracellular loop of CHRNB2. The mutation event can be a G412D substitution.

Example 1

Identification of Mutations in Ion Channels

Previous studies by reference (Wallace et al., 1998; PCT/AU01/00581; Wallace et al., 2001b; Australian patent AU-B-

56247/96; Steinlein et al., 1995; PCT/AU01/00541; Phillips et al., 2001; PCT/AU01/00729; PCT/AU01/01648; Wallace et al., 2001a, the disclosures of which are incorporated herein by reference) have identified mutations in a number of ion channel subunits associated with epilepsy. These include ion channel subunits of voltage-gated (eg SCN1A, SCN1B, KCNQ2, KCNQ3) or ligand-gated (eg CHRNA4, CHRNB2, GABRG2, GABRD) types. To identify further mutations in ion channel genes, subunits which comprise the ion channels were screened for molecular defects in epilepsy patients.

Human genomic sequence available from the Human Genome Project was used to characterize the genomic organisation for each subunit gene. Each gene was subsequently screened for sequence changes using single strand conformation polymorphism (SSCP) analysis in a large sample of epileptics with common sporadic IGE subtypes eg juvenile myoclonic epilepsy (JME), childhood absence epilepsy (CAE), juvenile absence epilepsy (JAE) and epilepsy with generalized tonic-clonic seizures (TCS). Clinical observations can then be compared to the molecular defects characterized in order to establish the combinations of mutant subunits involved in the various disease states, and therefore to provide validated drug targets for each of these disease states. This will provide a basis for novel drug treatments directed at the genetic defects present in each patient.

The coding sequence for each of the ion channel subunits was aligned with human genomic sequence present in available databases at the National Centre for Biotechnology Information (NCBI). The BLASTN algorithm was typically used for sequence alignment and resulted in the genomic organisation (intron-exon structure) of each gene being determined. Where genomic sequence for an ion channel subunit was not available, BACs or PACs containing the relevant ion channel subunit were identified through screening of high density filters containing these clones and were subsequently sequenced.

Availability of entire genomic sequence for each ion channel subunit facilitated the design of intronic primers spanning each exon. These primers were used for both high throughput SSCP screening and direct DNA sequencing.

Example 2

Sample Preparation for SSCP Screening

A large collection of individuals affected with epilepsy have undergone careful clinical phenotyping and additional data regarding their family history has been collated. Informed consent was obtained from each individual for blood collection and its use in subsequent experimental procedures. Clinical phenotypes incorporated classical IGE cases as well as GEFS+ and febrile seizure cases.

DNA was extracted from collected blood using the QIAamp DNA Blood Maxi kit (Qiagen) according to manufacturers specifications or through procedures adapted from Wyman and White (1980). Stock DNA samples were kept at a concentration of 1 ug/ul.

In preparation for SSCP analysis, samples to be screened were formatted into 96-well plates at a concentration of 30 ng/ul. These master plates were subsequently used to prepare exon specific PCR reactions in the 96-well format.

Example 3

Identification of Sequence Alterations in Ion Channel Genes

SSCP analysis of specific ion channel exons followed by sequencing of SSCP bandshifts was performed on individuals constituting the 96-well plates to identify sequence alterations.

Primers used for SSCP were labelled at their 5' end with HEX and typical PCR reactions were performed in a total volume of 10 µl. All PCR reactions contained 67 mM Tris-HCl (pH 8.8); 16.5 mM $(NH_4)_2SO_4$; 6.5 µM EDTA; 1.5 mM $MgCl_2$; 200 µM each dNTP; 10% DMSO; 0.17 mg/ml BSA; 10 mM β-mercaptoethanol; 5 µg/ml each primer and 100 U/ml Taq DNA polymerase. PCR reactions were performed using 10 cycles of 94° C. for 30 seconds, 60° C. for 30 seconds, and 72° C. for 30 seconds followed by 25 cycles of 94° C. for 30 seconds, 55° C. for 30 seconds, and 72° C. for 30 seconds. A final extension reaction for 10 minutes at 72° C. followed.

Twenty µl of loading dye comprising 50% (v/v) formamide, 12.5 mM EDTA and 0.02% (w/v) bromophenol blue were added to completed reactions which were subsequently run on non-denaturing 4% polyacrylamide gels with a cross-linking ratio of 35:1 (acrylamide:bis-acrylamide) and containing 2% glycerol. Gel thickness was 100 µm, width 168 mm and length 160 mm. Gels were run at 1200 volts and approximately 20 mA, at 22° C. and analysed on the GelScan 2000 system (Corbett Research, Australia) according to manufacturers specifications.

PCR products showing a conformational change were subsequently sequenced. This first involved re-amplification of the amplicon from the relevant individual (primers used in this instance did not contain 5' HEX labels) followed by purification of the PCR amplified templates for sequencing using QiaQuick PCR preps (Qiagen) based on manufacturers procedures. The primers used to sequence the purified amplicons were identical to those used for the initial amplification step. For each sequencing reaction, 25 ng of primer and 100 ng of purified PCR template were used. The BigDye sequencing kit (ABI) was used for all sequencing reactions according to the manufacturers specifications. The products were run on an ABI 377 Sequencer and analysed using the EditView program.

Table 1 shows the novel sequence changes identified in the ion channel subunits to date.

Example 4

Nicotinic Acetylcholine Receptor Mutations Outside M2 Domain

Initially, a rare variant (I225S) of the CHRNA4 subunit (also referred to as I257S) originally identified by Phillips et al., 1998) was examined functionally. Sequence analysis of the I225S CHRNA4 protein reveals that this amino acid change lies within the putative M1 segment of the protein and therefore raises the question of its possible effects on the receptor physiological properties. To examine possible receptor modifications, expression experiments in Xenopus oocytes were designed. However, because it is known that all patients that carry this mutation are heterozygous all experiments were carried out by co-expression of equal amounts of the patient control and mutated cDNA. Amplitude of the ACh-evoked currents evoked by saturating agonist concentrations showed no significant difference between the control and heterozygous expression. A marked difference was, however, observed when examining the receptor sensitivity to acetylcholine (ACh). Mutant containing receptors display a greater response at low ACh concentrations than their control counterpart. As previous functional studies of the first CHRNA4 mutation (S248F, Phillips et al., 1995) showed an increased receptor desensitization, the time course of the response for the I225S mutation was thoroughly monitored. Results showed that the average time course of the ACh-evoked current was not significantly different from the control and thereby suggests a minimal effect of this M1 mutation on the receptor desensitization properties.

Mutation screening by SSCP analysis of ADNFLE affected individuals has lead to the identification of a further 3 mutations in the CHRNA4 subunit gene that fall outside of the M2 domain (R336C, R369Q and P474R) as well as 4 new CHRNB2 mutations that also lie outside the M2 domain (T26M, L301V, V308A and G412D). To test the functional significance of these mutations the L301V CHRNB2 mutation was examined in *Xenopus* oocytes using similar approaches as for the I225S mutation in CHRNA4.

Results from these experiments showed that the L301V mutation caused no significant changes at the current amplitude evoked by saturating ACh concentration but a pronounced increased in agonist sensitivity was observed at the dose-response curve. In addition, the time course of the ACh-evoked current of the mutant receptors exhibits less desensitization.

The report of a naturally occurring mutation in a nAChR subunit associated with ADNFLE was the first genetic proof that ligand-gated channels cause seizures. Description of other mutations rapidly followed, demonstrating for the first time the role of nAChRs in brain function. Interestingly, the nAChR subunit mutations identified to date were all located inside or adjacent to the M2 domain of the protein. The common physiological trait observed between the mutant receptors is an increase in their sensitivity to ACh. In view of the distribution of mutations it was thought that only mutations in the M2 domain may lead to brain dysfunction.

The identification of two new, and spontaneously occurring, mutations that are outside the M2 domain raises new insights into the causes of ADFNLE. Despite the lack of crystallographic data for the transmembrane domain it is generally accepted that the M1 domain must be formed by an alpha-helix. Controversy exists, however, on the structure of the M3 domain and based on sequence homologies with other proteins it was proposed that the upper part of this transmembrane segment forms an alpha-helix while the lower part may form a beta-sheet. According to this model the CHRNB2 L301V mutation must be near the junction between the alpha-helix and the beta-sheet, a localization that may be critical for the overall protein structure.

Modifications to the nACh receptor functional properties were characterised as for the other mutations. Determination of the ACh dose-response curves revealed, as for the previously characterized nAChR mutants, a significant increase of the sensitivity of the mutant receptor compared to the control wild-type receptors. Comparison of the shift in ACh sensitivity of the nAChR mutations now studied functionally has revealed significant differences. Correlations between these changes in functional properties with either the disease penetrance or severity are, however, difficult to make in view of the restricted number of cases affected by each mutation.

Modification of the ACh sensitivity can be accompanied by an alteration of the response time course. Two possibilities can be envisaged with either an increase or a decrease in the desensitization profile. Examples of increased desensitization have already been reported for the CHRNA4 S248F or 776ins3 mutants (Bertrand et al., 1998). Averaging normalized responses of the CHRNA4 I225S mutant receptor readily illustrates that no significant modification of the response time course can be observed versus the controls recorded in the same batch of oocytes. In contrast, a significant reduction of the desensitization time course is observed for the CHRNB2 L301V mutant. Moreover, computing the maximal ACh evoked currents for the control and the L301V mutant revealed that cells expressing this mutant receptor display larger currents. While at present this increase in mean current can be attributed either to a higher level of protein expression or to a difference in single channel properties these data suggest that the L301V mutation causes a gain of function.

The number of distinct mutations associated with ADNFLE further illustrates the importance of the nAChRs in the triggering of seizures of patients suffering from this form of epilepsy. Constituting the first report of mutations localized outside the critical M2 segment the nAChR subunit mutants functionally characterized herein present the typical common trait of an increase in ACh sensitivity. These results indicate that mutations may occur in many different segments of the protein and therefore largely extend the probability of spontaneous occurrence. This probability is even higher, given that a mutation in either the CHRNA4 or CHRNB2 subunit is sufficient to cause a functional alteration of the receptor properties.

Methods

Mutation Analysis of CHRNB2

Single stranded conformation polymorphism (SSCP) analysis and sequencing were performed on individuals with epilepsy (ADNFLE) to identify disease causing mutations in the CHRNA4 and CHRNB2 genes.

Primers used for SSCP were labelled at their 5' end with HEX. The primers were designed within flanking CHRNA4 or CHRNB2 introns to enable amplification of each exon of the genes. Typical PCR reactions were performed in a total volume of 10 μl using 30 ng of patient DNA. PCR reactions were performed in 96 well plates or 0.5 ml tubes depending on batch size, and contained 67 mM Tris-HCl (pH 8.8); 16.5 mM $(NH_4)_2SO_4$; 6.5 μM EDTA; 1.5 mM $MgCl_2$; 200 μM each dNTP; 10% DMSO; 0.17 mg/ml BSA; 10 mM β-mercaptoethanol; 15 μg/ml each primer and 100 U/ml Taq DNA polymerase. PCR reactions were performed using 10 cycles of 94° C. for 30 seconds, 60° C. for 30 seconds, and 72° C. for 30 seconds followed by 25 cycles of 94° C. for 30 seconds, 55° C. for 30 seconds, and 72° C. for 30 seconds. A final extension reaction for 10 minutes at 72° C. followed. Twenty μl of loading dye comprising 50% (v/v) formamide, 12.5 mM EDTA and 0.02% (w/v) bromophenol blue were added to completed reactions which were subsequently run on non-denaturing 4% polyacrylamide gels with a cross-linking ratio of 35:1 (acrylamide:bis-acrylamide) and containing 2% glycerol. Gel thickness was 100 μm, width 168 mm and length 160 mm. Gels were run at 1200 volts and approximately 20 mA, at ambient temperature using the GelScan 2000 system (Corbett Research, Australia) according to manufacturers specifications. Results were subsequently analysed using the ONE-Dscan gel analysis software package (Scanalytics Inc.).

PCR products showing a conformational change were subsequently sequenced. This first involved re-amplification of the relevant amplicon using primers without the 5' HEX addition followed by purification of the PCR amplified templates for sequencing using QiaQuick PCR preps (Qiagen) based on manufacturers procedures. The primers used to sequence the purified nAChR subunit amplicons were identical to those used for the initial amplification step. For each sequencing reaction, 25 ng of primer and 100 ng of purified PCR template were used. The BigDye sequencing kit (ABI) was used for all sequencing reactions according to the manufacturers specifications. The products were run on an ABI 377 Sequencer and analysed using the EditView program.

The sequencing strategy revealed a number of nucleotide substitutions in both the CHRNA4 and CHRNB2 genes which were specific for affected individuals and not present in the normal population.

For CHRNA4, 3 epilepsy specific mutations were identified in the intracellular loop. These included a C→T transition at nucleotide position 1006 of the coding sequence, a G→A transition at nucleotide position 1106 of the coding sequence and a C→G transition at nucleotide position 1421 of the coding sequence. These nucleotide substitutions lead to R336C, R369Q and P474R amino acid changes respectively.

For CHRNB2, 4 epilepsy specific mutations were identified. These included a C→T transition at nucleotide position 77 of the coding sequence which lies in the signal sequence, a C→G transition at nucleotide position 901 and a T→C transition at nucleotide position 923 of the coding sequence which lie in the M3 domain, and a G→A transition at nucleotide position 1235 of the coding sequence. These nucleotide substitutions lead to T26M, L301V, V308A and G412D amino acid changes respectively.

*Xenopus* Oocyte Expression

Oocytes harvested from mature *Xenopus* females were isolated and prepared following standard methods (Bertrand, 1991). On the day following dissociation, oocytes were injected in their nucleus with 2 ng of cDNA expression vector. Mixtures of cDNAs were injected in equal quantity. To decrease the chance of contamination each oocyte was kept in a separate well of a 96-well microtiter plate (NUNC) at 18° C. During incubation time oocytes were kept in BARTH solution that contained: 88 mM NaCl, 1 mM KCl, 2.4 mM NaHCO$_3$, 10 mM HEPES, 0.82 mM MgSO$_4$ 7H$_2$O, 0.33 mM Ca(NO$_3$)$_2$.4H$_2$O, 0.41 mM CaCl$_2$.6H$_2$O, pH 7.4 adjusted with NaOH, and 100 unit/ml penicillin.

Recording of nAChR Properties

Two to three days after injection, oocytes were probed for their response to ACh. Oocytes were impaled with two electrodes and their electrophysiological properties determined using a two electrodes voltage-clamp (GENECLAMP amplifier, Axon Instruments, Forster City, Calif.). Electrodes were made of borosilicate capillary glass pulled with a BB-CH-PC puller (Mecanex, Switzerland), and filled with a filtered 3M KCl. During the experiments oocytes were continuously superfused with OR2 that contained: (82.5 mM NaCl, 2.5 mM KCl, 2.5 mM CaCl$_2$, 5 mM HEPES, pH 7.4 adjusted with NaOH). The flow was fed by gravity at approximately 6 ml/min and computer-driven electromagnetic valves controlled drug application. Unless specified, the holding potential was −100 mV and experiments were performed at 18° C.

Example 5

Digenic Model Examples

In some instances a single mutation in an ion channel alone is insufficient to give rise to an epilepsy phenotype. However combinations of mutations each conferring a subtle change of function to an ion channel, as proposed by the digenic model (PCT/AU01/00872), may be sufficient to produce an epilepsy phenotype.

Using the mutations and variations in ion channel subunits that form part of this invention, the digenic model may be validated through a parametric analysis of large families in which two abnormal alleles co-segregate by chance to identify mutations which act co-operatively to give an epilepsy phenotype. It is envisaged that the strategy of careful clinical phenotyping in these large families, together with a linkage analysis based on the digenic hypothesis will allow identification of the mutations in ion channels associated with IGEs. If molecular genetic studies in ICE are successful using the digenic hypothesis, such an approach might serve as a model for other disorders with complex inheritance.

The digenic hypothesis predicts that the closer the genetic relationship between affected individuals, the more similar the sub-syndromes, consistent with published data (Italian League Against Epilepsy Genetic Collaborative Group, 1993). This is because more distant relatives are less likely to share the same combinations of mutated subunits.

Identical twins have the same pair of mutated subunits and the same minor alleles so the sub-syndromes are identical. Affected sib-pairs, including dizygous twins, with the same sub-syndrome would also have the same pair of mutated subunits, but differences in minor alleles would lead to less similarity than with monozygous twins. Some sib-pairs and dizygous twins, have quite different sub-syndromes; this would be due to different combinations of mutated subunits, when the parents have more than two mutated alleles between them.

A special situation exists in inbred communities that parallels observations on autosomal recessive mouse models. Here the two mutated alleles of the digenic model are the same and thus result in a true autosomal recessive disorder. Because all affected individuals have the same pair of mutated alleles, and a similar genetic background, the phenotypes are very similar.

In outbred communities approximately 1% of the population would have IGE genotypes (2 mutated alleles) and 0.3% would clinically express IGE. Most of these would have mutations in two different channel subunits. In such communities most cases would appear "sporadic" as the risk to first degree relatives would be less than 10%.

For example, let there be three IGE loci (A, B, C) and let the frequency of abnormal alleles (a*, b*, c*) at each locus be 0.027 and of normal alleles (a, b, c) be 0.973. Then, the distribution of genotypes aa*, a*a, a*a* and aa at locus A will be 0.0263 (0.027×0.973), 0.0263, 0.0007 and 0.9467 respectively, and similarly for loci B and C. In this population 0.8485 will have no mutated alleles (0.9467$^3$), 0.1413 will have one mutated allele (a* or b* or c*; 0.0263×0.9467$^2$×6), 0.0098 will have two abnormal alleles (0.0020 two same abnormal alleles, 0.0078, two different abnormal alleles) and 0.00037 will have more than two abnormal alleles. Thus in this population 0.01, or 1%, will have two or more abnormal alleles (IGE genotype), and the total abnormal allele frequency will be 0.08 (3×0.027).

To determine the familial risks and allele patterns in affected pairs, the frequency distribution of population matings and the percentage of children with 2 or more abnormal alleles must be determined. The frequency of matings with no abnormal alleles (0×0) is 0.72 (0.8485$^2$), for 1×0 and 0×1 matings 0.24 (2×0.8485×0.1413), for a 1×1 mating 0.020, and for 2×0 and 0×2 matings 0.0166 etc. From this distribution of matings the frequency of children with 2 or more abnormal alleles can be shown to be 0.01. For example, the 0×2 and 2×0 matings contribute 0.0033 of this 0.01 frequency (0.0166[mating frequency]×0.2[chance of that mating producing a child with 2 or more abnormal alleles]).

To determine parental risk it can be shown that of children with 2 abnormal alleles (IGE genotype), 0.49 derive from 1×1 matings where no parent is affected, 0.33 derive from a 2×0 and 0×2 matings etc. For the 2×0 and 0×2 matings, half the parents have IGE genotypes and contribute 0.16 (0.33/2) to the parental risk with the total parental risk of an IGE genotype being 0.258. The other matings that contribute to affected parent-child pairs are 2×1, 1×2, 3×0, 0×3 etc.

The sibling risk of an IGE genotype is 0.305. For example 2×0 and 0×2 matings contributed 0.08 to the sibling risk (0.33[fraction of children with 2 abnormal alleles]×0.25[the chance of that mating producing a child with 2 or more abnormal alleles]). Similarly the offspring risk was determined to be 0.248 by mating individuals with 2 abnormal alleles with the general population. Thus at 30% penetrance the risk for IGE phenotype for parents of a proband is 0.077, for siblings 0.091, and for offspring 0.074.

It can be shown that affected sib pairs share the same abnormal allele pair in 85% of cases. This is because of all affected sib pairs 44% derive from 1×1 matings and 23% from 0×2 and 2×0 matings where all affected siblings have the same genotype. In contrast, 24% derive from 1×2 matings and 9% from 3×1 and 2×2 matings etc where affected sibling genotypes sometimes differ.

For affected parent-child pairs, genotypes are identical in only 58%. Of affected parent child pairs, 43% derive from 0×2 matings where genotypes are identical, whereas 38% derive from 0×3 and 17% from 1×2 where the majority of crosses yield different affected genotypes.

Based on the digenic model it has been postulated that most classical IGE and GEFS+ cases are due to the combination of two mutations in multi-subunit ion channels. These are typically point mutations resulting in a subtle change of function. The critical postulate is that two mutations, usually, but not exclusively, in different subunit alleles ("digenic model"), are required for clinical expression of IGE.

The hypothesis that similar phenotypes can be caused by the combination of mutations in two (or more) different subunits (outbred communities), or by the same mutation in two (or more) alleles of the same subunit (inbred communities), may seem implausible. However, applying the digenic hypothesis to the theoretical pentameric channel shown in FIG. 1, in outbred communities IGE will be due to subunit combinations such as $\alpha^*\alpha\beta^*\beta\Delta$, $\alpha^*\alpha^*\beta\beta\Delta^*$ or $\alpha\alpha\beta^*\beta\Delta^*$ (mutated subunits indicated by *). In inbred communities $\alpha^*\alpha^*\beta\beta\Delta$ or $\alpha\alpha\beta^*\beta^*\Delta$ combinations might cause IGE phenotypes. We assume that the mutations will not cause reduced expression of the alleles and that the altered ion channel excitability, and consequent IGE phenotype, caused by mutations in two different alleles is similar to that caused by the same mutation in both alleles of one subunit. Finally, subunit mutations with more severe functional consequences (eg breaking a disulphide bridge in SCN1B or amino acid substitution in the pore forming regions of SCN1A for GEFS+) cause autosomal dominant generalized epilepsies with a penetrance of 60-90%. Such "severe" mutations are rare (allele frequency <0.01%) and are infrequent causes of GEFS+. They very rarely, or perhaps never, cause classical IGE.

The relative separate segregation of classical IGE and GEFS+ phenotypes is an anecdotal clinical observation of ours (Singh et al., 1999), although the separation is not absolute. The separation is supported by previous family and EEG studies of Doose and colleagues who described "type A" and "type B" liabilities which we may approximate the GEFS+ and classical IGE groupings respectively (Doose and Baler, 1987).

The digenic model predicts that affected sib pairs will share the same genes in 85% of cases whereas they will have at least one different allele in the remaining 15%. In contrast, only 58% of parent-child pairs share the same alleles in a 3 locus model. Thus there should be greater similarity of syndromes between sibling pairs than parent-child pairs. This would be most objectively measured by age of onset and seizure types.

Estimates for the risk of febrile seizures or IGE in relatives vary. The estimates range from 5%-10% for siblings, 4%-6% for offspring, 3%-6% for parents, and 2-3% for grandparents. Underestimation may occur because IGE manifest in youth, and parents and particularly grandparents may be unaware of seizures in themselves in younger years. This is particularly true where there was stigma associated with epilepsy and where the epilepsy may have been mild and unrecognized. Underestimation of sibling and offspring risks occurs when unaffected young children are counted, some of whom will develop IGE in adolescence. Overestimation may occur with misdiagnosis of seizures or inclusion of seizures unrelated to IGE (e.g. due to trauma or tumors)

In autosomal dominant models the risk to affected relatives reduces proportionally (50% for first degree relatives, 25% for second degree etc). For all oligogenic or polygenic models the risk decreases more quickly. For a digenic model with three loci, the risks are 9.1% for siblings, 7.4% for offspring, 7.7% for parents. Rigorous measurement of the familial recurrence rates, with careful phenotyping and age-corrected risk estimates could be compared with the predictions from the digenic model, and it is proposed to do this.

There is a small amount of information on IGE families regarding haplotype distribution. For example, there is some evidence for a locus on 8q as determined by parametric linkage in a single family (Fong et al., 1998) and by non-parametric analysis in multiple small families (Zara et al., 1995). Interestingly, in the latter study the 8q haplotype not infrequently came from the unaffected parent. This would be quite compatible with the digenic model and evaluation of other data sets in this manner could be used to test the hypothesis, and it is proposed to do this.

Following the analysis of one large family with epilepsy where the two main phenotypes were childhood absence epilepsy (CAE) and febrile seizures (FS), the inheritance of FS was found to be autosomal dominant and the penetrance 75%. However the inheritance of CAE in this family was not simple Mendelian, but suggestive of complex inheritance with the involvement of more than one gene. The power of this large family was used to explore the complex genetics of CAE further.

Linkage analysis on this family in which individuals with CAE, FS and FS+ were deemed affected led to the detection of linkage on chromosome 5q and identification of a mutation in the GABRG2 gene (R43Q) which is localised to this region (Wallace et al., 2001a; PCT/AU01/00729). All 10 tested individuals with FS alone in this family had this mutation and 7 CAE affected individuals in this family also had the mutation. To test the digenic model of IGEs in the CAE affected individuals, the whole genome screen of this family was reanalysed with only individuals with CAE considered affected. Linkage analysis was performed using FASTLINK v4.0, two-point lod scores were calculated assuming 50% penetrance and a 2% phenocopy rate and individuals with FS or FS+ were coded as unknown. Markers producing a lod score greater than 1 were reanalysed without a phenocopy rate and at the observed penetrance for CAE in this family (30%). Results from the analysis revealed significant linkage to chromosome 14q22-q23 (lod 3.4). This provides strong evidence for a second locus segregating with CAE affected individuals in this family. While the GABRG2 mutation is sufficient to cause FS, the CAE phenotype is thought to be due to both the GABRG2 mutation and a mutation occurring in a gene mapping to the 14q locus, as proposed by the digenic model.

For the application of the digenic model to sporadic cases of IGE and affected individuals belonging to smaller families in which genotyping and linkage analysis is not a feasible approach to disease gene identification, direct mutation analysis of ion channel genes in these individuals has been carried out as described above. In Table 1 there is provided an indication of novel genetic alterations so far identified through mutation analysis screening of these individuals.

Figure 2:
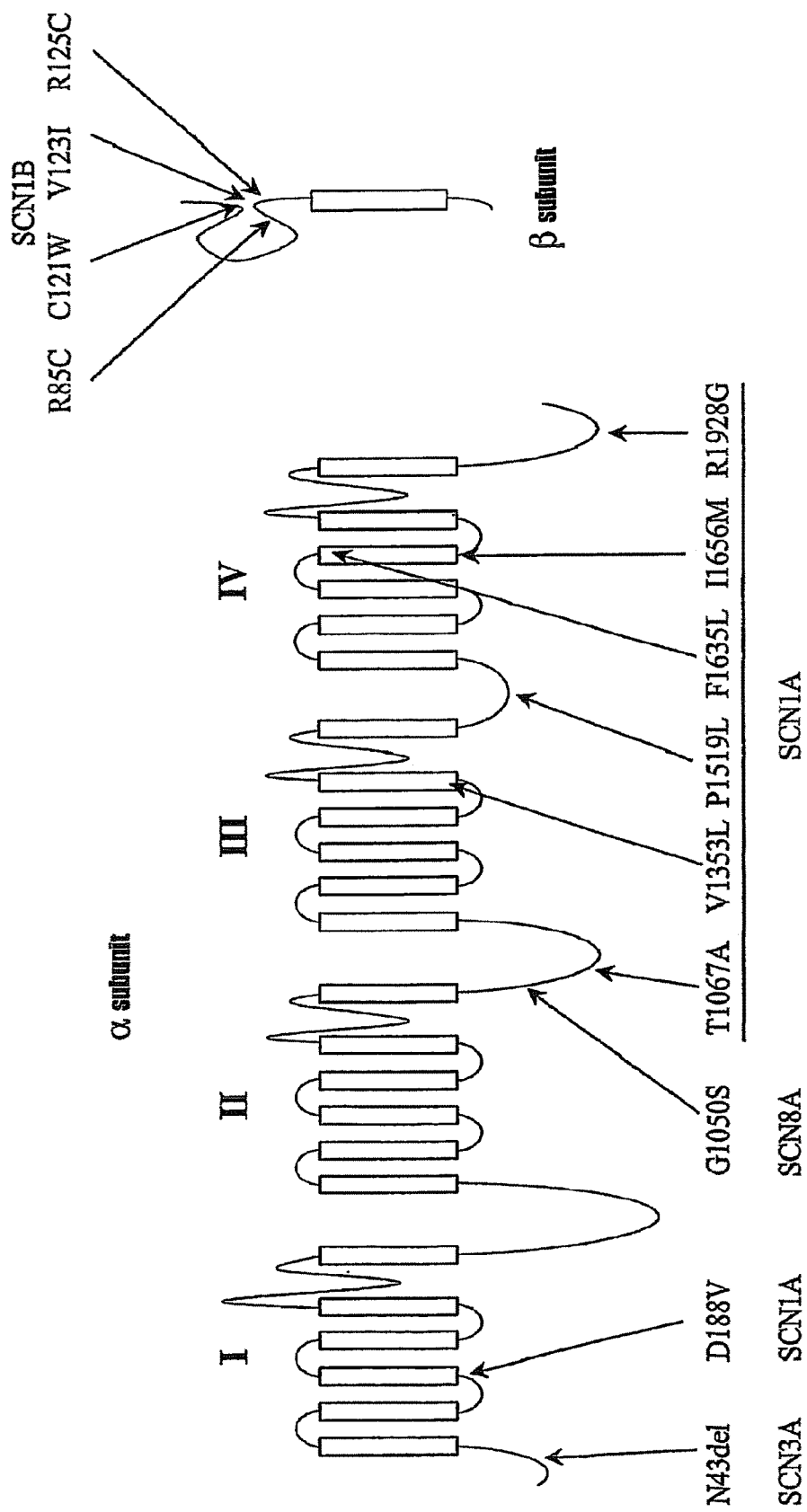
FIG. 2 represents the location of mutations identified in the ion channel subunits constituting the sodium channel. These examples include both novel and previously identified mutations.

FIG. 2 provides an example to indicate where some of these mutations have occurred with respect to the sodium channel genes.

The identification of novel mutations and variations in ion channel subunits in IGE individuals provides resources to further test the digenic hypothesis and mutation profiles are starting to accumulate for a number of subunit changes that are observed in the same individuals. FIG. 3 provides results from some of these profiles.

FIG. 3A shows a 3 generation family in which individual III-1 has myoclonic astatic epilepsy and contains a N43del mutation in the SCN3A gene as well as an A1067T mutation in the SCN1A gene. Individual I-1 also has the SCN3A mutation but alone this mutation is not sufficient to cause epilepsy in this individual. The SCN3A mutation has likely been inherited from the grandfather through the mother, while the SCN1A mutation is likely to arise from the father. Both parents are unaffected but have yet to be screened for the presence of the mutations in these subunits. Individual II-1 is likely to contain an as yet unidentified ion channel subunit mutation acting in co-operation with the SCN3A mutation already identified in this individual.

FIG. 3B is another 3 generation family in which individual III-1 has myoclonic astatic epilepsy due to a combination of the same SCN3A and SCN1A mutations as above. However, in this family both parents have febrile seizures most likely due to the presence of just one of the mutations in each parent, as proposed by the model. This is in contrast to individuals II-2 and II-3 in FIG. 4A who also contain one of the mutations in these genes each. These individuals are phenotypically normal most likely due to incomplete penetrance of these mutations in each case.

FIG. 3C shows a larger multi-generation family in which individual IV-5 has a mutation in both the SCN3A and GABRG2 subunits. In combination, these give rise to severe myoclonic epilepsy of infancy but alone either cause febrile seizures (GABRG2 mutation in III-3 and IV-4) or are without an effect (SCN3A mutation in III-2) as proposed by the model.

These examples therefore illustrate the digenic model as determined from mutation analysis studies of ion channel subunits in affected individuals and highlight the need to identify genetic alterations in the genes encoding ion channel subunits.

Example 6

Analysis of Receptors and Receptor Subunits

The following methods are used to determine the structure and function of the ion channels and ion channel subunits.
Molecular Biological Studies The ability of any one of the ion channels that form part of this invention to bind known and unknown proteins as a whole or through individual subunits can be examined. Procedures such as the yeast two-hybrid system are used to discover and identify any functional partners. The principle behind the yeast two-hybrid procedure is that many eukaryotic transcriptional activators, including those in yeast, consist of two discrete modular domains. The first is a DNA-binding domain that binds to a specific promoter sequence and the second is an activation domain that directs the RNA polymerase II complex to transcribe the gene downstream of the DNA binding site. Both domains are required for transcriptional activation as neither domain can activate transcription on its own. In the yeast two-hybrid procedure, the gene of interest or parts thereof (BAIT), is cloned in such a way that it is expressed as a fusion to a peptide that has a DNA binding domain. A second gene, or number of genes, such as those from a cDNA library (TARGET), is cloned so that it is expressed as a fusion to an activation domain. Interaction of the protein of interest with its binding partner brings the DNA-binding peptide together with the activation domain and initiates transcription of the reporter genes. The first reporter gene will select for yeast cells that contain interacting proteins (this reporter is usually a nutritional gene required for growth on selective media). The second reporter is used for confirmation and while being expressed in response to interacting proteins it is usually not required for growth.

Ion channel interacting genes may also be targets for mutation in epilepsy as well as other disorders associated with ion channel dysfunction. A mutation in an ion channel interacting gene when expressed alone, or when expressed in combination with one or more other ion channel mutations or ion channel interacting gene mutations (based on the digenic model), may give rise to the disorder. The nature of the ion channel interacting genes and proteins can be studied such that these partners can also be targets for drug discovery.
Structural Studies Ion channel recombinant proteins can be produced in bacterial, yeast, insect and/or mammalian cells and used in crystallographical and NMR studies. Together with molecular modelling of the protein, structure-driven drug design can be facilitated.

INDUSTRIAL APPLICABILITY

The mutant ion channel receptor subunits of the invention are useful in the diagnosis and treatment of diseases such as epilepsy and disorders associated with ion channel dysfunction including, but not limited to, hyper- or hypo-kalemic periodic paralysis, myotonias, malignant hyperthermia, myasthenia, cardiac arrhythmias, episodic ataxia, migraine, Alzheimer's disease, Parkinson's disease, schizophrenia, hyperekplexia, anxiety, depression, phobic obsessive symptoms, neuropathic pain, inflammatory pain, chronic/acute pain, Bartter's syndrome, polycystic kidney disease, Dent's disease, hyperinsulinemic hypoglycemia of infancy, cystic fibrosis, congenital stationary night blindness and total colour-blindness.

TABLE 1

Examples of mutations and variations identified in ion channel subunit genes

| Subunit Gene | Exon/Intron | DNA Mutation | Amino Acid Change | SEQ ID NOS |
|---|---|---|---|---|
| Sodium Channel Subunits Coding exonic variants - amino acid change | | | | |
| SCN1A$^r$ | Exon 1 | c111delC | P37fsX91 | 1, 135 |
| SCN1A$^{ra}$ | Exon 4 | c563A→T | D188V | |
| SCN1A$^r$ | Exon 9 | c1342-c1352del | I448X | 2, 136 |

TABLE 1-continued

Examples of mutations and variations identified in ion channel subunit genes

| Subunit Gene | Exon/Intron | DNA Mutation | Amino Acid Change | SEQ ID NOS |
|---|---|---|---|---|
| SCN1A[r] | Exon 20 | c3976G→C | A1326P | 3, 137 |
| SCN1A[ra] | Exon 21 | c4057G→C | V1353L | |
| SCN1A[r] | Exon 24 | C4556C→T | P1519L | 4, 138 |
| SCN1A[r] | Exon 26 | c4905C→G | F1635L | 5, 139 |
| SCN1A[ra] | Exon 26 | c4968C→G | I1656M | |
| SCN1A[r] | Exon 26 | c5363-c5364ins | N1788fsX1796 | 6, 140 |
| SCN1A[r] | Exon 26 | c5536-c5539delAAAC | S1846fsX1856 | 7, 141 |
| SCN1A[r] | Exon 26 | c5643G→C | E1881D | 8, 142 |
| SCN1A[r] | Exon 26 | c5870A→G | E1957G | 9, 143 |
| SCN8A[r] | Exon 14 | c3148G→A | G1050S | 10, 144 |
| SCN1B[ra] | Exon 3 | c253C→T | R85C | |
| SCN1B[ra] | Exon 3 | c363C→G | C121W | |
| SCN1B[r] | Exon 3 | c367G→A | V123I | 11, 145 |
| SCN1B[r] | Exon 3 | c373C→T | R125C | 12, 146 |
| SCN2A[r] | Exon 21 | c3988C→T | L1330F | 13, 147 |
| SCN2A[r] | Exon 25 | c4687C→G | L1563V | 14, 148 |
| SCN2A[r] | Exon 26 | c5465C→T | A1822V | 15, 149 |
| SCN1A[ca] | Exon 16 | c3199A→G | T1067A | |
| SCN1A[ca] | Exon 26 | c5782C→G | R1928G | |
| SCN8A[c] | Exon 14 | c3076C→T | R1026C | 16, 150 |
| SCN3A[c] | Exon 1 | c127-129delAAT | N43del | 17, 151 |
| Coding exonic variants - no amino acid change | | | | |
| SCN1A[r] | Exon 15 | c2889T→C | — | |
| SCN3A[r] | Exon 13 | c1971G→A | — | 18 |
| SCN3A[r] | Exon 27 | c5511C→T | — | 19 |
| SCN1A[c] | Exon 14 | c2522C→G | — | |
| SCN1A[c] | Exon 26 | c5418G→A | — | 20 |
| SCN3A[c] | Exon 13 | c1884T→A | — | 21 |
| SCN3B[c] | Exon 3 | c438C→T | — | 22 |
| Non-coding variants | | | | |
| SCN1A[r] | Intron 8 | IVS8(-9-10)delTT | — | 23 |
| SCN1A[r] | Intron 10 | IVS10-47T→G | — | 24 |
| SCN1A[r] | Intron 18 | IVS18+1G→A | — | 25 |
| SCN1A[r] | Intron 22 | IVS22-14T→G | — | 26 |
| SCN8A[r] | Intron 6 | IVS6+9C→T | — | 27 |
| SCN3A[r] | Intron 23 | IVS23-31delT | — | 28 |
| SCN8A[c] | Intron 15 | IVS15+20G→A | — | 29 |
| SCN1B[c] | Intron 1 | IVS1+15G→T | — | 30 |
| Nicotinic Acetylcholine Receptor Subunits | | | | |
| Coding exonic variants - amino acid change | | | | |
| CHRNA4[r] | Exon 5 | c770T→G | I257S | 31, 152 |
| CHRNA4[ra] | Exon 5 | c839C→T | S280F | |
| CHRNA4[r] | Exon 5 | c1006C→T | R336C | 32, 153 |
| CHRNA4[r] | Exon 5 | c1106G→A | R369Q | 33, 154 |
| CHRNA4[r] | Exon 5 | c1421C→G | P474R | 34, 155 |
| CHRNB2[r] | Exon 2 | c77C→T | T26M | 35, 156 |
| CHRNB2[ra] | Exon 5 | c859G→A | V287M | |
| CHRNB2[r] | Exon 5 | c901C→G | L301V | 36, 157 |
| CHRNB2[r] | Exon 5 | c923T→C | V308A | 134, 173 |
| CHRNB2[r] | Exon 5 | c1235G→A | G412D | 37, 158 |
| CHRNB2[c] | Exon 5 | c1191G→C | Q397H | 38, 159 |
| Coding variants - no amino acid change | | | | |
| CHRNA4[r] | Exon 5 | c978C→T | — | 39 |
| CHRNA4[r] | Exon 5 | c1104C→T | — | 40 |
| CHRNA4[r] | Exon 5 | c1635G→A | — | 41 |
| CHRNA4[c] | Exon 1 | c51G→A | — | 42 |
| CHRNA4[c] | Exon 5 | c1629C→T | — | 43 |
| CHRNA4[c] | Exon 5 | c1659G→A | — | 44 |
| CHRNB2[r] | Exon 2 | c78G→A | — | 45 |
| CHRNB2[r] | Exon 2 | c109C→T | — | 46 |
| CHRNB2[r] | Exon 5 | c825G→A | — | 47 |
| CHRNB2[c] | Exon 5 | c1233G→A | — | 48 |
| CHRNB2[r] | Exon 6 | c1482A→G | — | 49 |
| Non-coding variants | | | | |
| CHRNA4[c] | Intron 5 | IVS5+11C→T | — | 50 |
| CHRNA4[c] | Intron 5 | IVS5+14G→A | — | 51 |
| CHRNB2[c] | Intron 5 | IVS5+14G→A | — | 52 |

TABLE 1-continued

Examples of mutations and variations identified in ion channel subunit genes

| Subunit Gene | Exon/Intron | DNA Mutation | Amino Acid Change | SEQ ID NOS |
|---|---|---|---|---|
| Potassium Channel Subunits | | | | |
| Coding exonic variants - amino acid change | | | | |
| KCNQ3[r] | Exon 15 | c2306C→A | P769H | 53, 160 |
| KCNQ2[c] | Exon 15 | c2255C→A | T752N | 54, 161 |
| Coding exonic variants - no amino acid change | | | | |
| KCNQ5[r] | Exon 14 | c1869A→T | — | 55 |
| KCNQ2[c] | Exon 6 | c912C→T | — | 56 |
| KCNQ2[c] | Exon 11 | c1419C→G | — | 57 |
| KCNQ2[c] | Exon 15 | c2154T→A | — | 58 |
| KCNQ2[c] | Exon 15 | c2460G→A | — | 59 |
| KCNQ3[c] | Exon 4 | c660T→C | — | 60 |
| KCNQ3[c] | Exon 4 | c732T→C | — | 61 |
| KCNQ3[c] | Exon 7 | c1071C→G | — | 62 |
| Non-coding variants | | | | |
| KCNQ2[r] | Intron 11 | IVS11+1G→A | — | 63 |
| GABA Receptor Subunits | | | | |
| Coding exonic variants - amino acid change | | | | |
| GABRD[r] | Exon 5 | c530A→C | E177A (E129A) | 64, 162 |
| GABRD[ra] | Exon 6 | c658C→T | R220C (R172C) | |
| GABRG2[ra] | Exon 2 | c245G→A | R82Q (R43Q) | |
| GABRG2[ra] | Exon 9 | c1168C→T | Q390X (Q351X) | |
| GABRA6[r] | Exon 2 | c136C→T | R46W (R27W) | 65, 163 |
| GABRPi[r] | Exon 2 | c28G→A | V10M | 66, 164 |
| GABRE[r] | Exon 2 | c196G→A | G66S (G48S) | 67, 165 |
| GABRD[c] | Exon 6 | c659G→A | R220H (R172H) | 68, 166 |
| GABRA6[c] | Exon 9 | c1210C→T | P385S | 69, 167 |
| GABRA5[c] | Exon 5 | c235A→C | I79L (I48L) | 70, 168 |
| GABRA4[c] | Exon 1 | c76C→A | L26M (signal peptide) | 71, 169 |
| GABRA4[c] | Exon 8 | c1063A→G | T355A (T320A) | 72, 170 |
| GABRB3[b] | Exon 1A | c(exon1A)31C→T | P11S | 73, 171 |
| GABRE[c] | Exon 2 | c113A→G+c154G→A | Y38C + E52K | 74, 172 |
| Coding exonic variants - no amino acid change | | | | |
| GABRB3[r] | Exon 6 | C603C→T | — | 75 |
| GABRB3[r] | Exon 7 | c783G→A | — | 76 |
| GABRB3[r] | Exon 8 | c1005C→T | — | 77 |
| GABRB3[r] | Exon 9 | c1293G→A | — | 78 |
| GABRA1[r] | Exon 11 | c1155C→A | — | 79 |
| GABRA1[r] | Exon 11 | c1440A→G | — | 80 |
| GABRA4[r] | Exon 8 | c1095T→C | — | 81 |
| GABRD[r] | Exon 4 | c405C→T | — | 82 |
| GABRD[r] | Exon 4 | c444C→T | — | 83 |
| GABRA2[r] | Exon 7 | c513G→A | — | 84 |
| GABRPi[r] | Exon 2 | c19T→C | — | 85 |
| GABRPi[r] | Exon 2 | c51G→A | — | 86 |
| GABRB3[c] | Exon 1A | c(exon1A)75C→T | — | 87 |
| GABRB1[c] | Exon 8 | c846A→G | — | 88 |
| GABRA1[c] | Exon 4 | c156T→C | — | 89 |
| GABRD[c] | Exon 4 | c330C→T | — | 90 |
| GABRD[c] | Exon 7 | c816C→T | — | 91 |
| GABRD[c] | Exon 9 | c1104C→T | — | 92 |
| GABRG2[c] | Exon 3 | c315C→T | — | 93 |
| GABRG2[c] | Exon 5 | c588T→C | — | 94 |
| GABRA2[c] | Exon 6 | c396G→A | — | 95 |
| GABRA6[c] | Exon 8 | c1005G→C | — | 96 |
| GABRA5[c] | Exon 8 | c606T→C | — | 97 |
| GABRA5[c] | Exon 10 | c975T→C | — | 98 |
| GABRG1[c] | Exon 3 | c264A→G | — | 99 |
| GABRG1[c] | Exon 11 | c1459G→A | — | 100 |
| GABRE[c] | Exon 2 | c186G→A | — | 101 |
| GABA Receptor Subunits | | | | |
| Non-coding variants | | | | |
| GABRA1[r] | Exon 2 | c-53C→A | — | 102 |
| GABRA2[r] | 5' UTR | c-(-9-10)delAG | — | 103 |
| GABRB2[r] | 5' UTR | c-(-213G→A | — | 104 |
| GABRB2[r] | Intron 1 | IVS1-(-8-9)insT | — | 105 |
| GABRA2[r] | Intron 9 | IVS9+149G→T | — | 106 |
| GABRD[r] | Intron 4 | IVS4+45delG | — | 107 |
| GABRD[r] | Intron 6 | IVS6+92G→T | — | 108 |
| GABRD[r] | Intron 6 | IVS6+73C→T | — | 109 |
| GABRG3[r] | Intron 5 | IVS5+20C→T | — | 110 |

TABLE 1-continued

Examples of mutations and variations identified in ion channel subunit genes

| Subunit Gene | Exon/Intron | DNA Mutation | Amino Acid Change | SEQ ID NOS |
|---|---|---|---|---|
| GABRG2[r] | Intron 1 | IVS1+12C→T | — | 111 |
| GABRB1[r] | Intron 2 | IVS2−51C→A | — | 112 |
| GABRA5[r] | Intron 6 | IVS6+10G→C | — | 113 |
| GABRA3[r] | Intron 5 | IVS5+26-29delGTCT | — | 114 |
| GABRPi[r] | Intron 1 | IVS1−85C→T | — | 115 |
| GABRPi[r] | Intron 4 | IVS4−85T→A | — | 116 |
| GABRPi[r] | Intron 7 | IVS7+8A→C | — | 117 |
| GABRA3[c] | Intron 3 | IVS3−(19-20)insT | — | 118 |
| GABRA4[c] | Intron 1 | IVS1−10delT | — | 119 |
| GABRA4[c] | Intron 1 | IVS1−(10-11)insT | — | 120 |
| GABRA4[c] | Intron 1 | IVS1−(10-11)delTT | — | 121 |
| GABRA5[c] | Intron 9 | IVS9−9A→C | — | 122 |
| GABRB2[c] | Intron 1 | IVS1−8delT | — | 123 |
| GABRB2[c] | Intron 1 | IVS1−(-8-9)delTT | — | 124 |
| GABRG3[c] | Intron 1 | IVS1+11C→T | — | 125 |
| GABRB3[c] | Intron 8 | IVS8+15A→G | — | 126 |
| GABRD[c] | Intron 1 | IVS1−17A→G | — | 127 |
| GABRD[c] | Intron 8 | IVS8−7C→T | — | 128 |
| GABRD[c] | Intron 8 | IVS8−14C→T | — | 129 |
| GABRB2[c] | Intron 6 | IVS6−11T→C | — | 130 |
| GABRB3[c] | Intron 3 | IVS3+13C→A | — | 131 |
| GABRA3[c] | Intron 1 | IVS1−21-22insT | — | 132 |
| GABRB3[c] | Exon 1 | c(exon1)−43G→A | — | 133 |

Note:
[a]Mutations or variations previously reported in publications and patent applications (all other mutations or variations are otherwise novel);
[r]Mutations or variations only occurring in individuals with epilepsy;
[b]Variant seen only in normal control samples;
[c]Mutations or variants seen in individuals with epilepsy as well as normal control samples.
Numbers in brackets represent amino acid changes corresponding to numbering based on the mature protein sequence.

REFERENCES

References cited herein are listed on the following pages, and are incorporated herein by this reference.

Andermann, E. (1982). In: *Genetic basis of the epilepsies*. Anderson, V E. Hauser, W A. Penry, J K. and Singh, C F. (Editors). New York, Raven Press. 355-374.

Annegers, J F. (1996). *The treatment of epilepsy: Principles and practice*. Second Edition. (Wyllie E (Ed) Williams and Wilkins).

Bell, J I. and Lathrop, M. (1996). *Nature Genet.* 13: 377-378.

Berkovic, S F. Andermann, F. Andermann, E. and Gloor, P. (1987). *Neurology* 37: 993-1000.

Berkovic, S F. Reutens, D C. Andermann, E. and Andermann, F. (1994). In: *Epileptic seizures and syndromes*. Wolf, P. (Editor). London: John Libbey. 25-37.

Berkovic, S F. Mazarib, A. Neufeld, M. et al. (2000). *Neurology (Supplement 3).* 54: A356.

Biervert, C. Schroeder, B C. Kubisch, C. Berkovic, S F. Propping, P. Jentsch, T J. and Steinlein, O K. (1998). *Science* 279: 403-406.

Cavazzuti, G B. Capella, L. and Nalin, A. (1980). *Epilepsia* 21: 43-55.

Charlier, C. Singh, N A. Ryan, S G. Lewis, T B. Reus, B E. Leach, R J. and Leppert, M. (1998). *Nature Genet.* 18: 53-55.

Cole, S P. Campling, B G. Atlaw, T. Kozbor, D. and Roder, J C. (1984). *Mol. Cell Biochem.* 62: 109-120.

Collins, F S. (1995). *Nature Genet.* 9: 347-350.

Commission on Classification and Terminology of the International League against Epilepsy. (1989). *Epilepsia* 30: 389-399.

Cote, R J. Morrissey, D M. Houghton, A N. Beattie, E J Jr. Oettgen, H F. and Old, L J. (1983). *Proc. Natl. Acad. Sci. USA* 80: 2026-2030.

Doose, H. and Baier, W K. (1987). *Neuropediatrics* 18 (Supplement 1): 1-64.

Doose, H. and Baier, W. (1989). *Clev. Clin. J. Med.* 56 (Supplement): s105-s110.

Dworakowska, B. and Dolowy, K. (2000). *Acta Biochim. Pol.* 47: 685-703.

Escayg, A. MacDonald, B T. Meisler, M H. Baulac, S. Huberfeld, G. An-Gourfinkel, I. Brice, A. LeGuern, E. Moulard, B. Chaigne, D. Buresi, C. and Malafosse, A. (2000). *Nature Genet.* 24: 343-345.

Fong, G C. Shah, P U. Gee, M N. Serratosa, J M. Castroviejo, I P. Khan, S. Ravat, S H. Mani, J. Huang, Y. Zhao, H Z. Medina, M T. Treiman, L J. Pineda, G. and Delgado-Escueta, A V. (1998). *Am. J. Hum. Genet.* 63: 1117-1129.

Gardiner, M. (2000). *J Neurol.* 247: 327-334.

Goldman, C K. Soroceanu, L. Smith, N. Gillespie, G Y. Shaw, W. Burgess, S. Bilbao, G. and Curiel, D T. (1997). *Nature Biotechnology* 15: 462-466.

Gonzalez, J E. et al. (1999). *Drug Discov. Today* 4: 431-439.

Greenberg, D A. Delagado-Escueta, A V. Maldonado, H M. and Widelitz, H. (1988a). *Genet Epidem.* 5: 81-94.

Greenberg, D A. Delgado-Escueta, A V. Widelitz, H. Sparkes, R S. Treiman, L. Maldonado, H M. Park, M S. and Terasaki, P I. (1988b). *Am. J. Med. Genet.* 31: 185-192.

Hamill, O P. et al. (1981). *Pflugers Arch.* 391: 85-100.

Hauser, W A. Annegers, J F. and Kurland, L T. (1993). *Epilepsia* 34: 453-468.

Heller, R A. Schena, M. Chai, A. Shalon, D. Bedilion, T. Gilmore, J. Woolley, D E. and Davis R W. (1997). *Proc. Natl. Acad. Sci. USA* 94: 2150-2155.

Huse, W D. Sastry, L. Iverson, S A. Kang, A S. Alting-Mees, M. Burton, D R. Benkovic, S J. and Lerner, R A. (1989). *Science* 246: 1275-1281.

Italian League Against Epilepsy Genetic Collaborative Group. (1993). *Epilepsia* 34: 819-26.

Janz, D. Beck-Mannagetta, G. and Sander, T. (1992). *Neurology* 42 (Supplement 5): 48-55.

Kohler, G. and Milstein, C. (1975). *Nature* 256: 495-497.

Kozbor, D. Abramow-Newerly, W. Tripputi, P. Cole, S P. Weibel, J. Roder, J C. and Croce, C M. (1985). *J. Immunol. Methods* 81:31-42.

Lernmark, A. and Ott, J. (1998). *Nature Genet.* 19: 213-214.

Okubo, Y. Matsuura, M. Asai, T. Asai, K. Kato, M. Kojima, T. and Toru, M. (1994). *Epilepsia* 35: 832-841.

Orlandi, R. Gussow, D H. Jones, P T. and Winter, G. (1989). *Proc. Natl. Acad. Sci. USA* 86: 3833-3837.

Panayiotopoulos, C P. and Obeid, T. (1989). *Ann. Neurol.* 25: 440-443.

Phillips, H A. Favre, I. Kirkpatrick, M. Zuberi, S M. Goudie, D. Heron, S E. Scheffer, I E. Sutherland, G R. Berkovic, S F. Bertrand, D. and Mulley, J C. (2001). *Am. J. Hum. Genet.* 68: 225-231.

Reutens, D C. and Berkovic, S F. (1995). *Neurology* 45: 1469-1476.

Risch, N. and Botstein, D. (1996). *Nature Genet.* 12: 351-353.

Roger, J. Bureau, M. Dravet, C. Dreifuss, F E. Perret, A. and Wolf, P. (1992). *Epileptic syndromes in infancy, childhood and adolescence.* 2nd Edition. London, John Libbey.

Scharf, K D. Materna, T. Treuter, E. and Nover, L. (1994). *Results Probl. Cell Differ.* 20: 125-162.

Scheffer, I E. and Berkovic, S F. (1997). *Brain* 120: 479-90.

Schena, M. Shalon, D. Heller, R. Chai, A. Brown, P O. and Davis, R W. (1996). *Proc. Natl. Acad. Sci. USA* 93: 10614-10619.

Singh, N A. Charlie, C. Stauffer, D. DuPont, B R. Leach, R J. Melis, R. Ronen, G M. Bjerre, I. Quattlebaum, T. Murphy, J V. McHarg, M L. Gagnon, D. Rosales, T O. Peiffer, A. Anderson, V E. and Leppert, M. (1998). *Nature Genet.* 18: 25-29.

Singh, R. Scheffer, I E. Crossland, K. and Berkovic, S F. (1999). *Ann. Neurol.* 45: 75-81.

Steinlein, O K. Mulley, J C. Propping, P. Wallace, R H. Phillips, H A. Sutherland, G R. Scheffer, I E. and Berkovic, S F. (1995). *Nature Genet.* 11: 201-203.

Todd, J A. (1999). *Lancet* 354 (Supplement 1): 15-16.

Wallace, R H. Marini, C. Petrou, S. Harkin, L A. Bowser, D N. Panchal, R G. Williams, D A. Sutherland, G R. Mulley, J C. Scheffer, I E. and Berkovic, S F. (2001a). *Nature Genet.* 28: 49-52.

Wallace, R H. Scheffer, I E. Barnett, S. Richards, M. Dibbens, L. Desai, R R. Lerman-Sagie, T. Lev, D. Mazarib, A. Brand, N. Ben-Zeev, B. Goikhman, I. Singh, R. Kremmidiotis, G. Gardner, A. Sutherland, G R. George, A L Jr. Mulley, J C. and Berkovic, S F. (2001b). *Am. J. Hum. Genet.* 68: 859-865.

Wallace, R H. Wang, D W. Singh, R. Scheffer, I. George, A. Phillips, H. Saar, K. Reis, A. Johnson, E. Sutherland, G. Berkovic, S. and Mulley, J. (1998). *Nature Genet.* 19: 366-370.

Winter, G. and Milstein, C. (1991). *Nature* 349: 293-299.

Wyman, A R. and White, R. (1980). *Proc. Natl. Acad. Sci.* 77: 6754-6758.

Zara, F. Bianchi, A. Avanzini, G. Di Donato, S. Castellotti, B. Patel, P I. and Pandolfo, M. (1995). *Hum. Mol. Genet.* 4: 1201-1207.

Zara, F. Gennaro, E. Stabile, M. Carbone, I. Malacarne, M. Majello, L. Santangelo, R. de Falco, F A. and Bricarelli, F D. (2000). *Am. J. Hum. Genet.* 66: 1552-1557.

---

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07989182B2). An electronic copy of the "Sequence Listing" will also be available from the USPTO upon request and payment of the fee set forth in 37 CFR 1.19(b)(3).

---

What is claimed is:

1. An isolated nucleic acid molecule comprising the nucleotide sequence of SEQ ID NO.: 1.

2. An isolated nucleic acid molecule consisting of the nucleotide sequence of SEQ ID NO.: 1.

3. An isolated expression vector comprising a nucleic acid molecule as claimed in claim 1 or claim 2.

4. An isolated cell comprising one or more expression vectors claimed in claim 3.

5. A method of preparing a polypeptide encoded by a nucleic acid as claimed in claim 1 or claim 2, comprising the steps of:
   (1) culturing cells under conditions effective for polypeptide production, wherein the cells comprise one or more expression vectors comprising a nucleic acid molecule as claimed in claim 1 or claim 2; and
   (2) harvesting the polypeptide.

\* \* \* \* \*